United States Patent
Vaillant et al.

(10) Patent No.: US 7,995,819 B2
(45) Date of Patent: Aug. 9, 2011

(54) METHODS FOR DISPLAYING A LOCATION OF A POINT OF INTEREST ON A 3-D MODEL OF AN ANATOMICAL REGION

(75) Inventors: Regis Vaillant, Villebon sur Yvette (FR); Elisabeth Soubelet, Meudon (FR); Jasbir Singh Sra, Pewaukee, WI (US)

(73) Assignee: General Electric Company, Schenectady, NY (US)

( * ) Notice: Subject to any disclaimer, the term of this patent is extended or adjusted under 35 U.S.C. 154(b) by 950 days.

(21) Appl. No.: 11/928,759

(22) Filed: Oct. 30, 2007

(65) Prior Publication Data

US 2008/0152205 A1 Jun. 26, 2008

Related U.S. Application Data

(60) Provisional application No. 60/855,115, filed on Oct. 30, 2006.

(51) Int. Cl.
*G06K 9/00* (2006.01)

(52) U.S. Cl. .............................. 382/128; 128/922; 378/4

(58) Field of Classification Search .................. 382/100, 382/128, 129, 130, 131, 132; 128/922; 378/4–27
See application file for complete search history.

(56) References Cited

U.S. PATENT DOCUMENTS

| | | | |
|---|---|---|---|
| 6,333,960 B1 * | 12/2001 | Tam | 378/15 |
| 6,359,960 B1 * | 3/2002 | Wahl et al. | 378/20 |
| 6,603,870 B1 * | 8/2003 | Bascle | 382/132 |
| 6,907,100 B2 * | 6/2005 | Taguchi | 378/4 |
| 6,923,768 B2 | 8/2005 | Camus et al. | |
| 7,197,107 B2 * | 3/2007 | Arai et al. | 378/20 |
| 2002/0154801 A1 | 10/2002 | Ohishi | |
| 2005/0027193 A1 * | 2/2005 | Mitschke et al. | 600/427 |
| 2006/0078195 A1 * | 4/2006 | Vaillant et al. | 382/154 |
| 2006/0079759 A1 | 4/2006 | Vaillant et al. | |

OTHER PUBLICATIONS

Co-pending U.S. Appl. No. 11/928,484, filed Oct. 30, 2007, entitled Method for Generating a Registered Image Relative to a Cardiac Cycle and a Respiratory Cycle of a Person.

* cited by examiner

*Primary Examiner* — Anand Bhatnagar
(74) *Attorney, Agent, or Firm* — Cantor Colburn LLP

(57) ABSTRACT

Methods for displaying a location of a point of interest on a 3-D model of an anatomical region of a person are provided. In one exemplary embodiment, the method includes generating first and second 2-D images of the anatomical region utilizing an image acquisition system when an X-ray source of the image acquisition system is disposed at first and second positions, respectively, in a 3-D coordinate system of the image acquisition system. The method further includes selecting first and second points in the first and second 2-D images, respectively. The method further includes utilizing a triangulation technique utilizing the first and second points to determine a point of interest in a 3-D coordinate system of the 3-D model of the anatomical region.

16 Claims, 29 Drawing Sheets

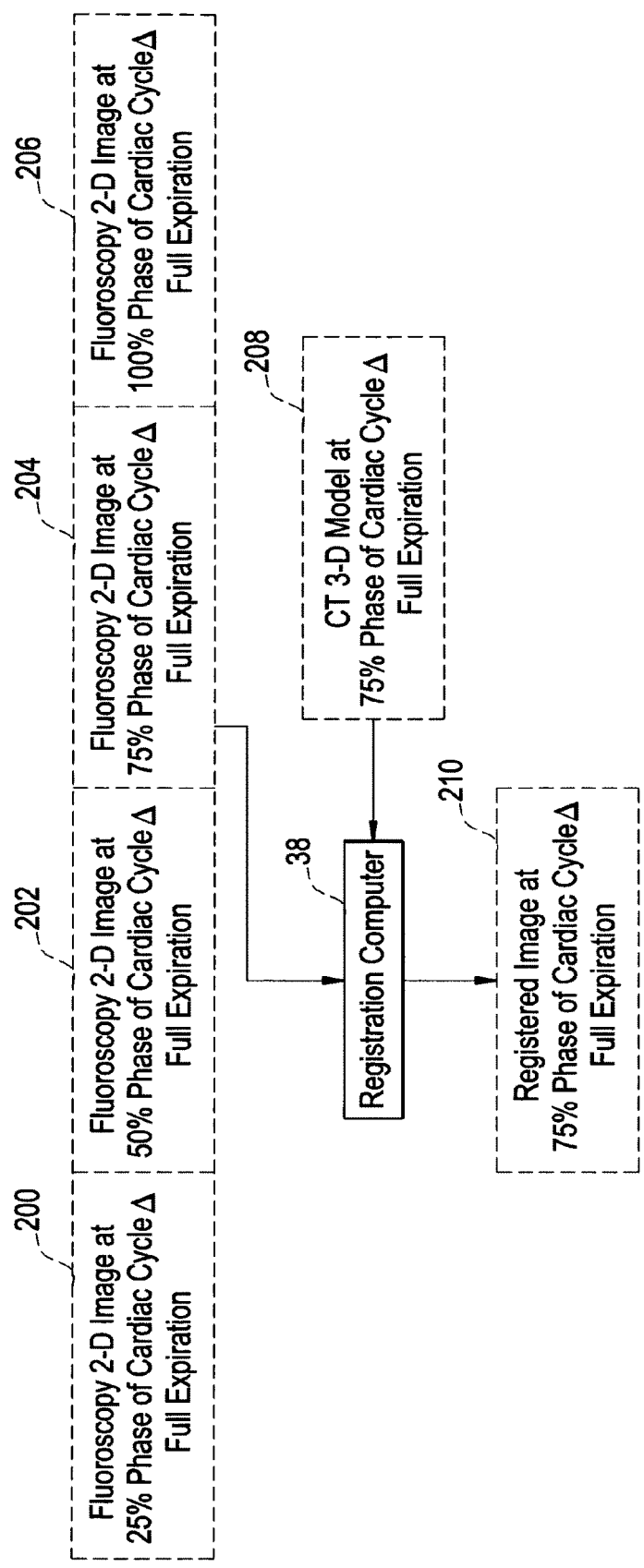

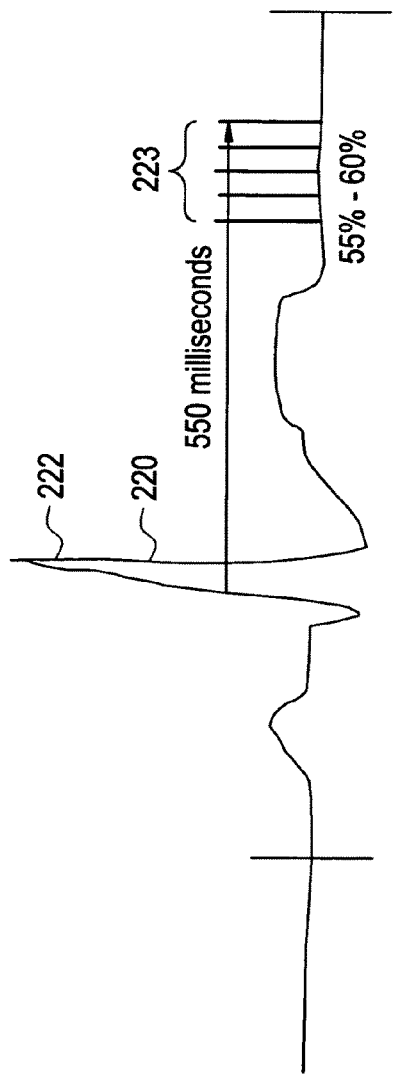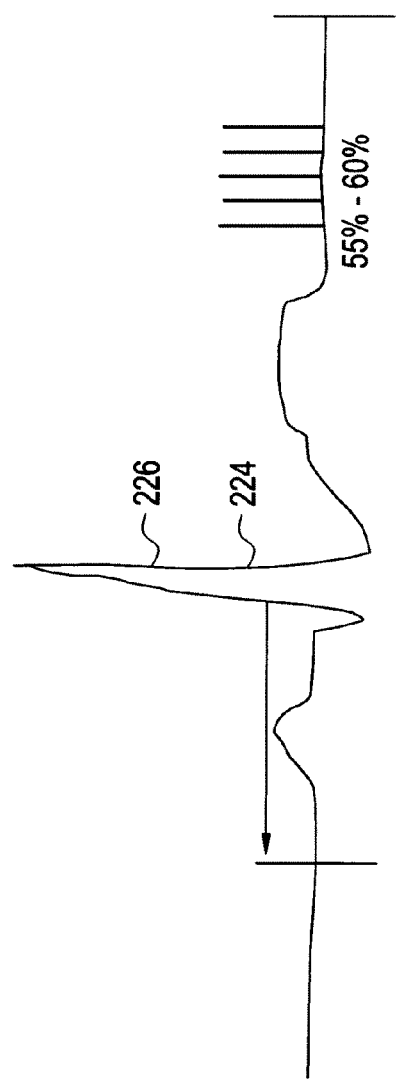

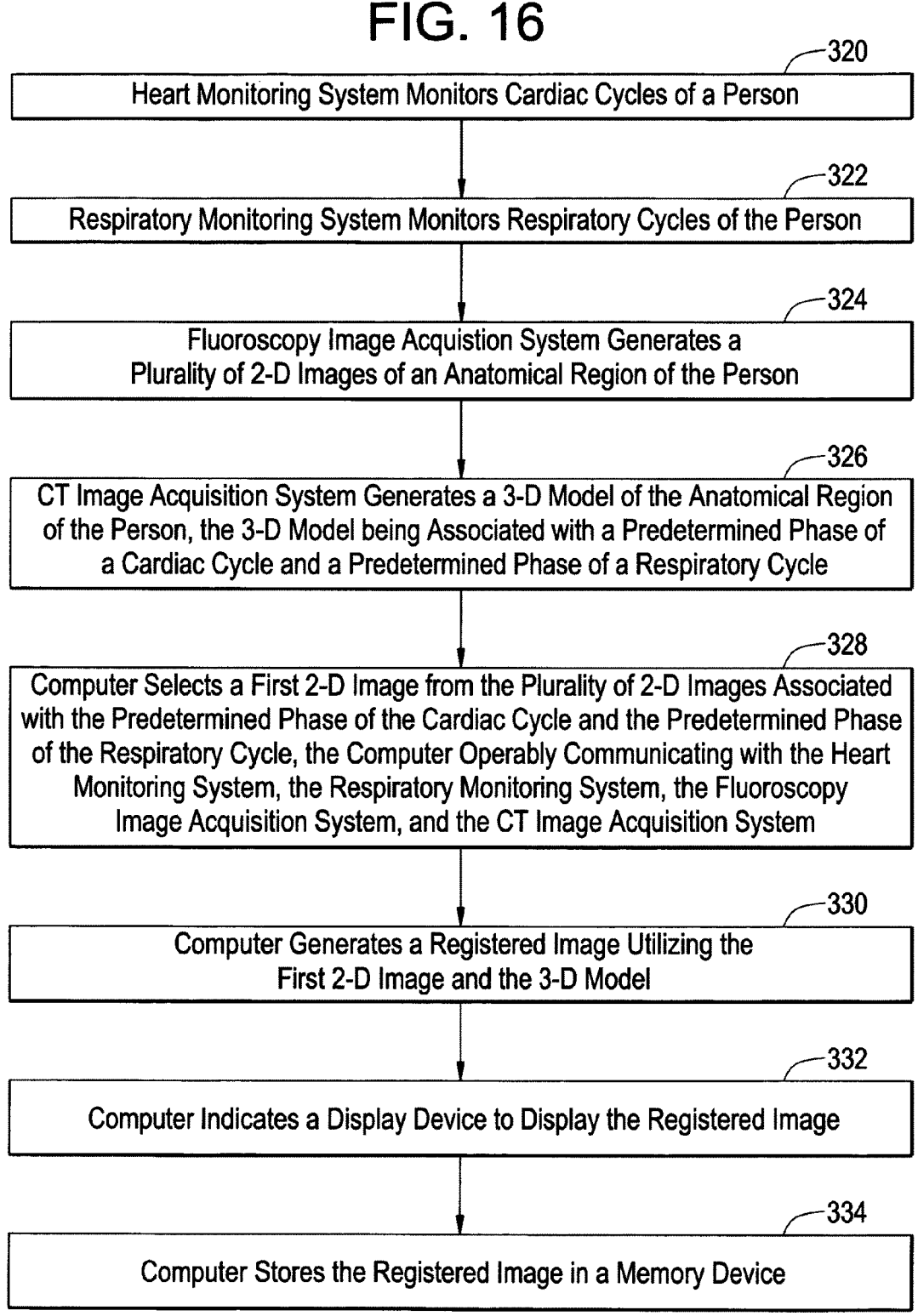

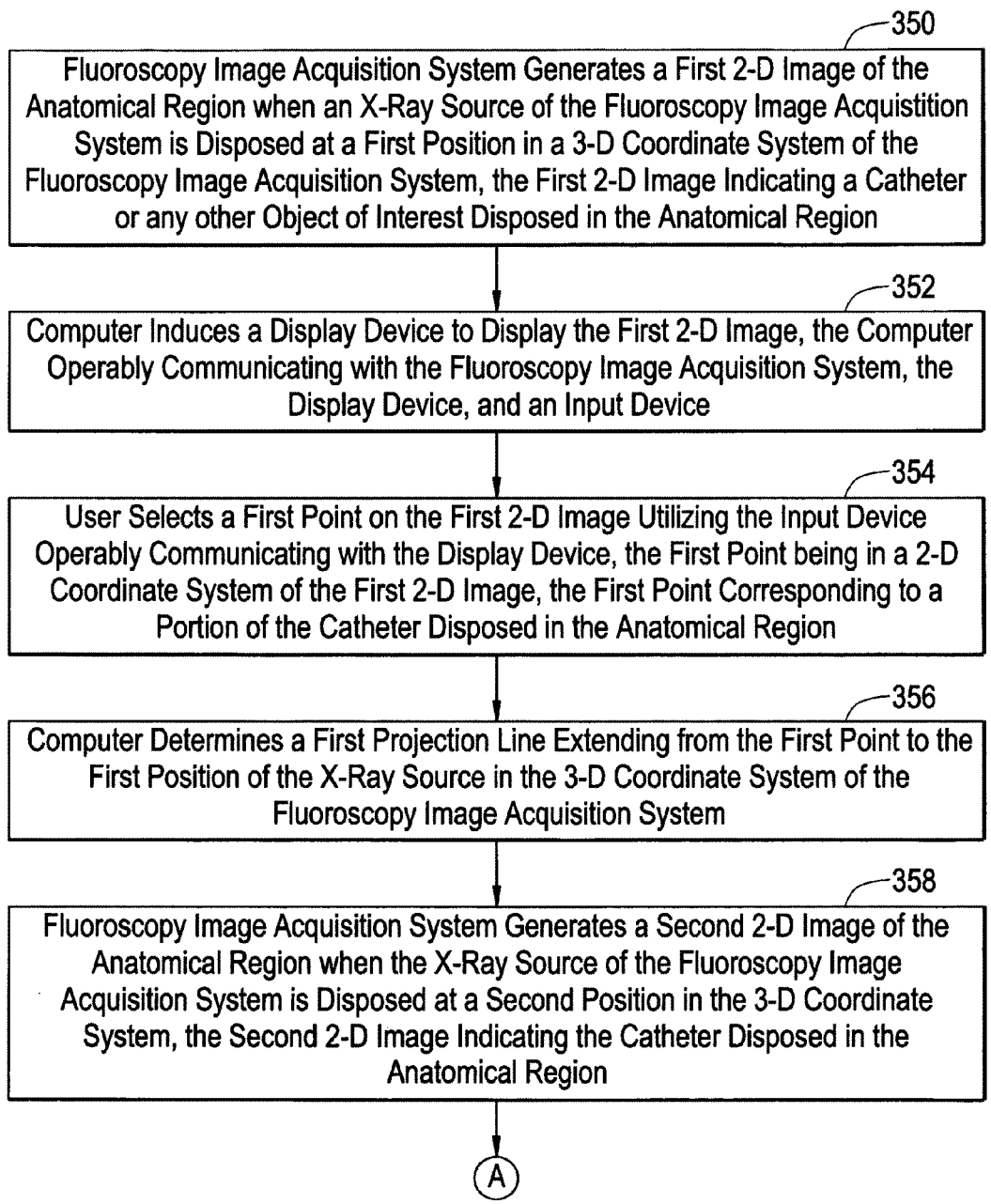

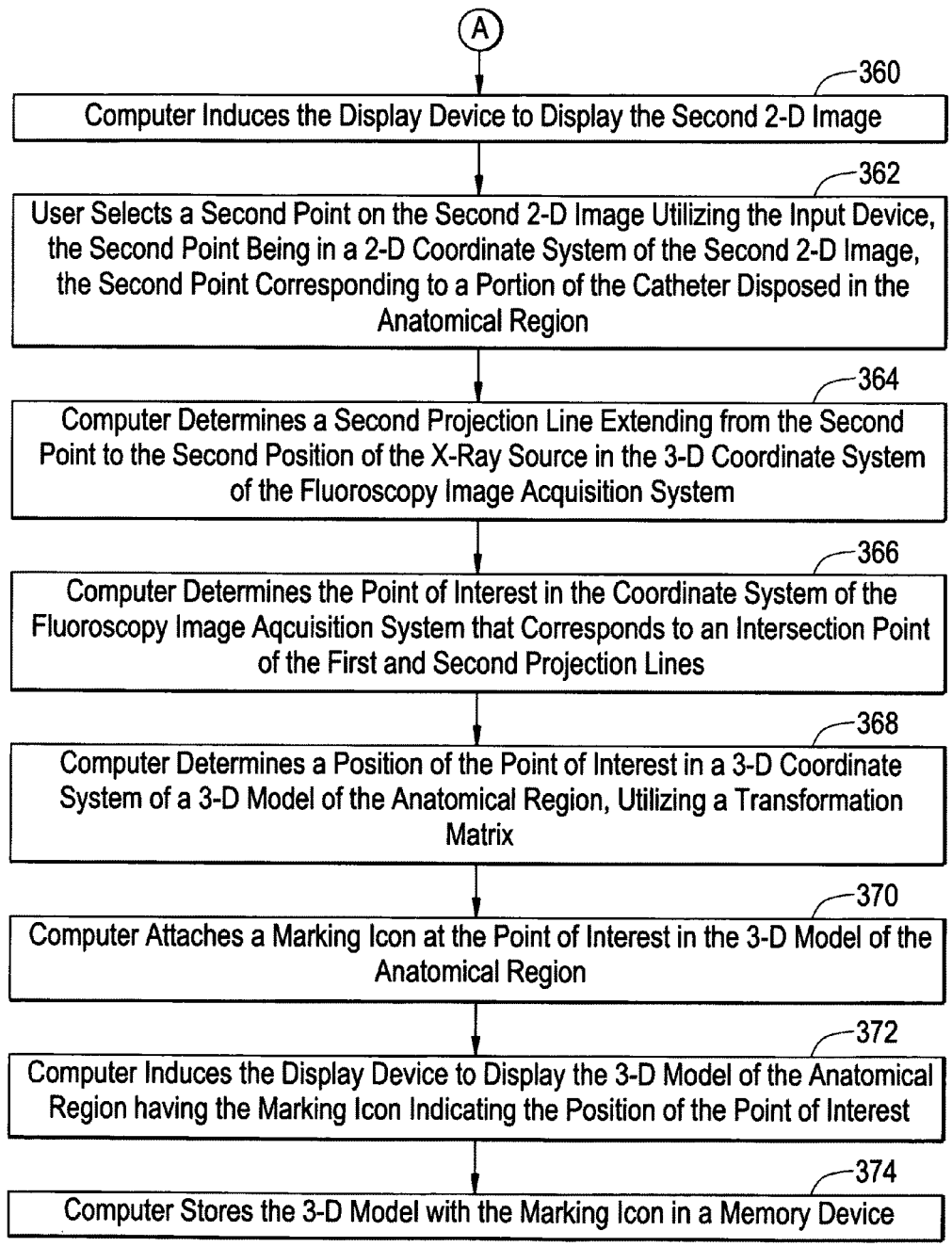

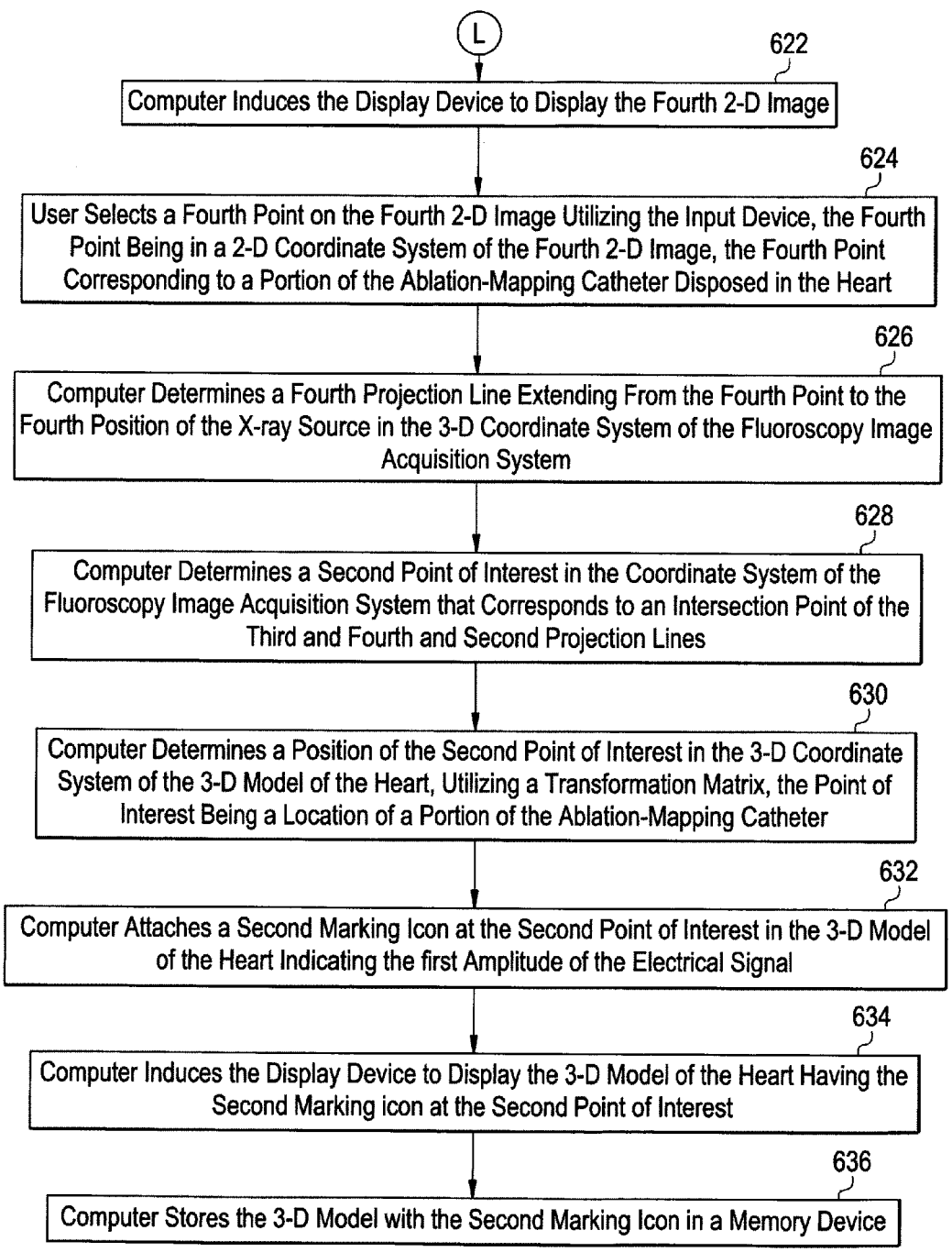

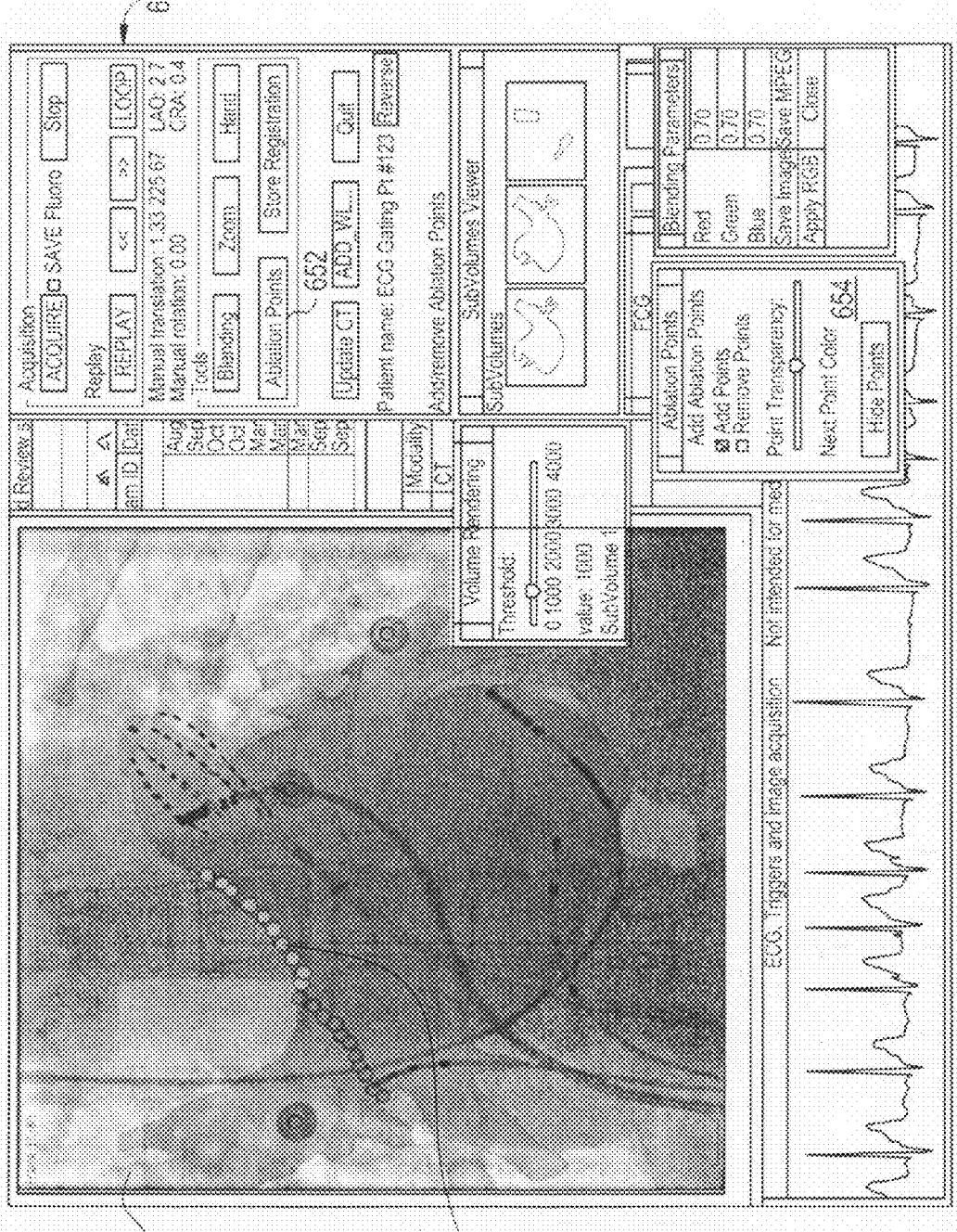

Antero posterior view

METHODS FOR DISPLAYING A LOCATION OF A POINT OF INTEREST ON A 3-D MODEL OF AN ANATOMICAL REGION

CROSS REFERENCE TO RELATED APPLICATION

The application claims the benefit of U.S. Provisional application, Ser. No. 60/855,115, filed Oct. 30, 2006, the contents of which are incorporated herein by reference thereto.

BACKGROUND OF THE INVENTION

A fluoroscopy system has been utilized to generate a 2-D image of an anatomical region. Further, a CT system has been utilized to generate a 3-D model an anatomical region. However, a drawback associated with the fluoroscopy system and the CT system, is that a point of interest identified on a 2-D image cannot be automatically identified in a 3-D model of the anatomical region.

The inventors herein have recognized a need for a method for displaying a location of a point of interest on a 3-D model of an anatomical region, utilizing at least one point on at least one 2-D image of the anatomical region.

BRIEF DESCRIPTION OF THE INVENTION

A method for displaying a location of a point of interest on a 3-D model of an anatomical region of a person in accordance with an exemplary embodiment is provided. The method includes determining a first projection line extending from a first point on a first 2-D image to a first position of an X-ray source. The first point is in a 2-D coordinate system of the first 2-D image. The first position is in the 3-D coordinate system of an image acquisition system. The method further includes determining a second projection line extending from a second point on a second 2-D image to a second position of the X-ray source. The second point is in a 2-D coordinate system of the second 2-D image. The second position is in the 3-D coordinate system of the image acquisition system. The method further includes determining the point of interest in the 3-D coordinate system of the image acquisition system that corresponds to an intersection point of the first and second projection lines. The method further includes determining a position of the point of interest in a 3-D coordinate system of the 3-D model of the anatomical region. The method further includes displaying the 3-D model of the anatomical region on a display device. The 3-D model has a marking icon at the point of interest.

A method for displaying a location of a point of interest on a 3-D model of an anatomical region of a person in accordance with another exemplary embodiment is provided. The method includes generating a first 2-D image of the anatomical region when an X-ray source is disposed at a first position in a 3-D coordinate system of a 3-D model of the anatomical region. The method further includes selecting a first point on the first 2-D image relative to a 2-D coordinate system of the first 2-D image. The method further includes projecting the 3-D model in a first projection direction to obtain a first projected image. The method further includes determining a second point on the first projected image corresponding to the first point on the first 2-D image, utilizing a first transformation matrix. The method further includes determining a first projection line extending from the second point to the first position of the X-ray source in the 3-D coordinate system of the 3-D model. The method further includes generating a second 2-D image of the anatomical region when the X-ray source is disposed at a second position in the 3-D coordinate system of the 3-D model. The method further includes selecting a third point on the second 2-D image of the anatomical region relative to a 2-D coordinate system of the second 2-D image. The method further includes projecting the 3-D model in a second projection direction to obtain a second projected image. The method further includes determining a fourth point on the second projected image corresponding to the third point on the second 2-D image, utilizing a second transformation matrix. The method further includes determining a second projection line extending from the fourth point to the second position of the X-ray source in the 3-D coordinate system of the 3-D model. The method further includes determining the point of interest in the 3-D coordinate system of the 3-D model that corresponds to an intersection point of the first and second projection lines. The method further includes displaying the 3-D model of the anatomical region on a display device. The 3-D model has a marking icon at the point of interest.

A method for displaying a location of a point of interest on a 3-D model of an anatomical region of a person in accordance with another exemplary embodiment is provided. The method includes generating a 2-D image of the anatomical region utilizing an image acquisition system when an X-ray source of the image acquisition system is disposed at a first position in a 3-D coordinate system of a 3-D model of the anatomical region. The method further includes selecting a point on the 2-D image relative to a 2-D coordinate system of the 2-D image. The method further includes determining a first projection line extending from the point on the 2-D image to the first position of the X-ray source in the 3-D coordinate system of the 3-D model. The method further includes determining at least first and second points on the 3-D model where the first projection line intersects an outer surface of the 3-D model. The method further includes selecting one of the first and second points representing the location of the point of interest. The method further includes displaying the 3-D model of the anatomical region on a display device. The 3-D model has a marking icon at the selected one of the first and second points representing the point of interest.

BRIEF DESCRIPTION OF THE DRAWINGS

FIG. 8 is a block diagram of a method for generating a registered image utilizing cardiac gating and respiratory gating;

FIG. 9 is a schematic of an exemplary ECG signal;

FIG. 10 is another schematic of an exemplary ECG signal;

FIG. 16 is a flowchart of a method for generating a registered image in accordance with another exemplary embodiment;

FIGS. 17-18 are flowcharts of a method for displaying a location of a point of interest on a 3-D model of an anatomical region of a person in accordance with another exemplary embodiment;

FIGS. 27-31 are flowcharts of a method for displaying a location of a point of interest on a 3-D model of an anatomical region of a person;

FIG. 32 is a schematic of a graphical user interface for identifying a location of the point of interest on a 3-D model of an anatomical region of a person;

DETAILED DESCRIPTION OF THE INVENTION

Figure 1:
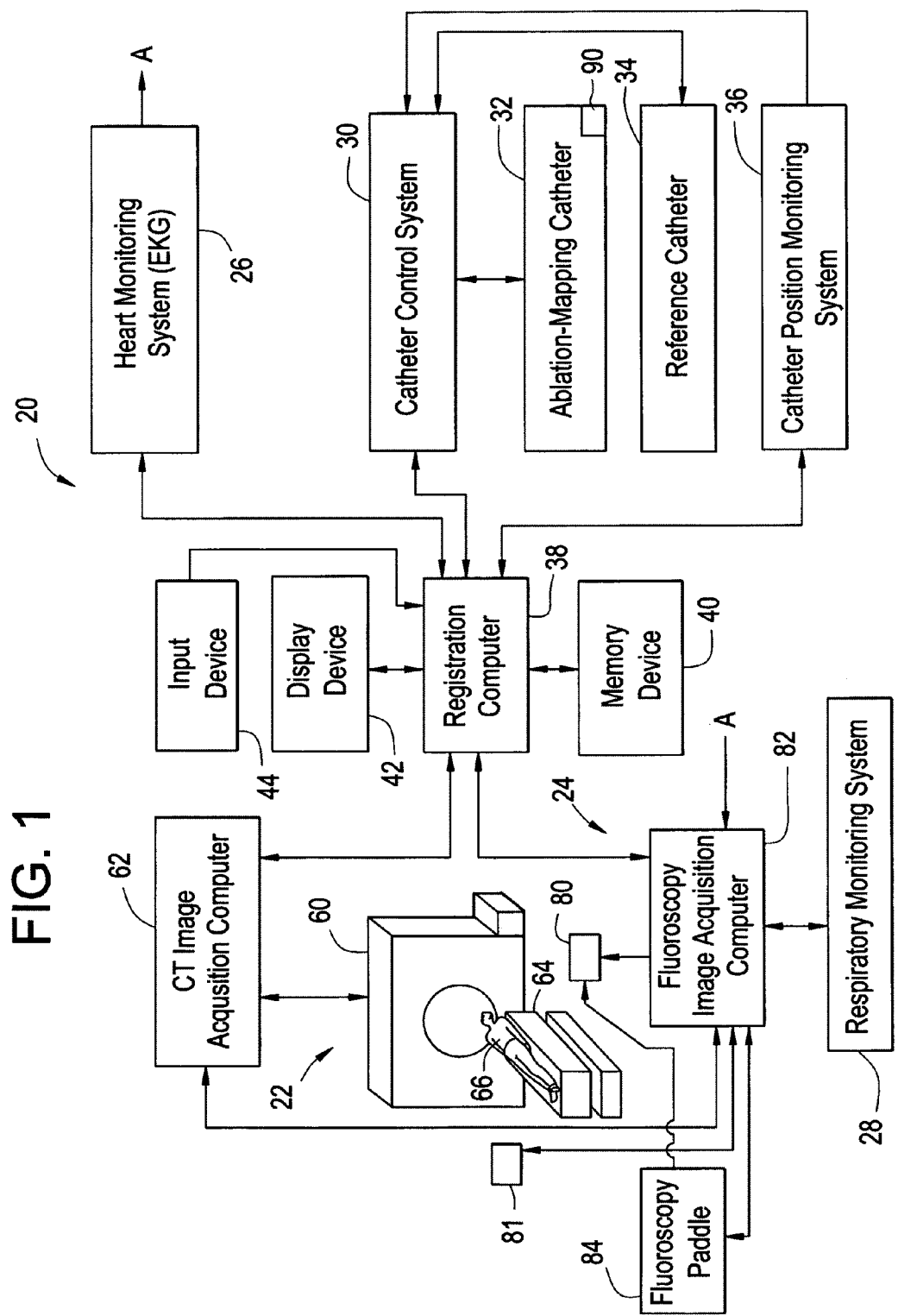
FIG. 1 is a schematic of a system for displaying a location of a point of interest on a 3-D model of an anatomical region and for generating a registered image in accordance with an exemplary embodiment.

Referring to FIG. 1, a schematic of a system 20 for displaying a location of a point of interest on a 3-D model of an anatomical region and for generating a registered image in accordance with an exemplary embodiment is illustrated. The system 20 includes a computed tomography (CT) image acquisition system 22, a fluoroscopy image acquisition system 24, a heart monitoring system 26, a respiratory monitoring system 28, a catheter control system 30, and ablation-mapping catheter 32, a reference catheter 34, a catheter position monitoring system 36, a registration computer 38, a memory device 40, a display device 42, and an input device 44.

The CT image acquisition system 22 is provided to generate a 3-D model of the anatomical region of a person 66. The CT image acquisition system 22 includes a CT scanning device 60, a CT image acquisition computer 62, and a table 64. The CT scanning device 60 generates scanning data of the anatomical region of the person 66 who is disposed on the table 64. The CT scanning device 60 transfers the scanning data to the CT image acquisition computer 62. Thereafter, the CT image acquisition computer 62 generates a 3-D model of the anatomical region of the person 66 based on the scanning data. Further, the CT image acquisition computer 62 can transfer the 3-D model of the anatomical region to the registration computer 38. The CT image acquisition computer 62 operably communicates with the registration computer 38 and the fluoroscopy image acquisition computer 82. It should be noted that in alternative embodiments, other types of systems other than the CT image acquisition system 22 can be utilized to generate 3-D models of the anatomical region. For example, in alternative embodiments, a magnetic resonance imaging (MRI) image acquisition system or an ultrasonic image acquisition system could be utilized to generate a 3-D model of the anatomical region.

The fluoroscopy image acquisition system 24 is provided to generate a plurality of 2-D images of the anatomical region of a person 66. In one exemplary embodiment, the fluoroscopy image acquisition system 24 can generate a 2-D image of the anatomical region during a predetermined phase of the cardiac cycle and a predetermined phase of a respiratory cycle, based on a control signal from the registration computer 38. The fluoroscopy image acquisition system 24 includes an X-ray source 80, an X-ray detector 81, a fluoroscopy image acquisition computer 82, and a fluoroscopy paddle 84. When the fluoroscopy paddle 84 is depressed by operator, the X-ray source 80 generates X-rays that propagate through the anatomical region of the person 66. The X-ray detector 81 detects the X-rays that have propagated through the person 66 and generates data that is transferred to the fluoroscopy image acquisition computer 82. The fluoroscopy image acquisition computer 82 generates 2-D images of the anatomical region utilizing the data from the X-ray detector 81. In one exemplary embodiment, the fluoroscopy image acquisition computer 82 generates 2-D images of the anatomical region in response to a control signal received from the registration computer 38 indicating that the person has a predetermined phase of a cardiac cycle and predetermined phase of a respiratory cycle. The fluoroscopy image acquisition computer 82 can transfer the 2-D images of the anatomical region to the registration computer 38. The fluoroscopy image acquisition computer 82 operably communicates with the registration computer 38, the fluoroscopy paddle 84, the X-ray source 80, the X-ray detector 81, and the respiratory monitoring system 28.

It should be noted that the inventors herein have recognized a computer system can more accurately locate a point of interest on a 3-D model of an anatomical region, utilizing one or more points selected on one or more 2-D images of the anatomical region, when the 3-D model and the 2-D images correspond to a predetermined phase of a cardiac cycle and a predetermined phase of a respiratory cycle.

Referring to FIGS. 1 and 9, the heart monitoring system 26 is provided to generate an ECG signal indicative of a cardiac cycle of the person 66. The registration computer 38 can utilize an ECG signal 220 to instruct the fluoroscopy image acquisition computer 82 to generate 2-D images when the heart has a predetermined phase of a cardiac cycle, which is referred to as cardiac gating. Alternately, the registration computer 38 can utilize intracardiac electrograms obtained from the catheters such as the coronary sinus catheter positioned inside of the heart, to instruct the fluoroscopy image acquisition computer 82 to generate 2-D images when the heart has a predetermined phase of a cardiac cycle. As shown, the ECG signal 220 has a QRS complex portion 222 and an atrial diastole portion 223 (i.e., relaxation phase of the heart).

In one exemplary embodiment, the fluoroscopy image acquisition system 24 generates 2-D images of the anatomical region when the ECG signal 220 indicates a cardiac phase range of 55-60% of the cardiac cycle. In another exemplary embodiment, the fluoroscopy image acquisition system 24 generates 2-D images of the anatomical region when the ECG signal 220 indicates a ventricular diastole (i.e., a cardiac phase range of 70-75% of the cardiac cycle). Of course, other cardiac phases or phase ranges could be utilized by the fluoroscopy image acquisition system 24 to generate 2-D images.

Referring to FIG. 9, a priori technique for determining a time for generating 2-D images during a predetermined phase of a cardiac cycle will be explained. Initially, the ECG signal 220 is monitored for several heart beats (e.g., 10 heart beats). Thereafter, an average rate of these beats is calculated to determine the next time interval in the priori technique. Further, an R wave is calculated and a degree of prematurity is also taken into account. For example, any beat within 50% of the average period of the beats is considered premature and ignored. In case of irregular rhythm such as atrial fibrillation this evaluation is ignored. An ECG trigger timer (shown by an arrow in FIG. 9) is started when an amplitude of the ECG signal 220 at the QRS complex portion is greater than a predetermined amplitude. The leading (rising) edge of the QRS complex portion 222 is a positive slope and trailing (falling) edge of the QRS complex portion 222 is a negative slope. It is noted that the priori method prevents acquisition of a 2-D image on a T wave. Further, a refractory time period, such as 200-300 milliseconds for example, is determined when the trailing edge of the QRS complex portion 222 is less than the threshold amplitude. During the refractory period, the fluoroscopy image acquisition computer 82 does not generate new 2-D images. As illustrated, the ECG signal 220 represents an average R-R interval of 10 heart beats was 1000 milliseconds (60 beats) per minute. In this example, when the ECG trigger timer measures 550 milliseconds, a heart is at the 55% phase of the cardiac cycle. Alternately, when the ECG trigger timer measures 750 milliseconds, a heart is at the 75% phase of the cardiac cycle.

Referring to FIG. 10, a post priori technique can also be utilized to determine a time for generating 2-D images during a predetermined phase of a cardiac cycle. In particular, a preceding heart beat is selected and either a 55% phase or a 75% phase of the cardiac cycle is determined based on the preceding heart beat.

Referring to FIG. 1, the respiratory monitoring system 28 is provided to determine a phase of a respiratory cycle of the person 66. The respiratory monitoring system utilizes 2-D images generated by the fluoroscopy image acquisition system 24 to determine a phase of the respiratory cycle, as will be explained below. The registration computer 38 can utilize data representing the phase of the respiratory cycle from the respiratory monitoring system 28 to instruct the fluoroscopy image acquisition computer 82 to generate 2-D images during a predetermined phase of the respiratory cycle, which is referred to as respiratory gating.

Figure 12:
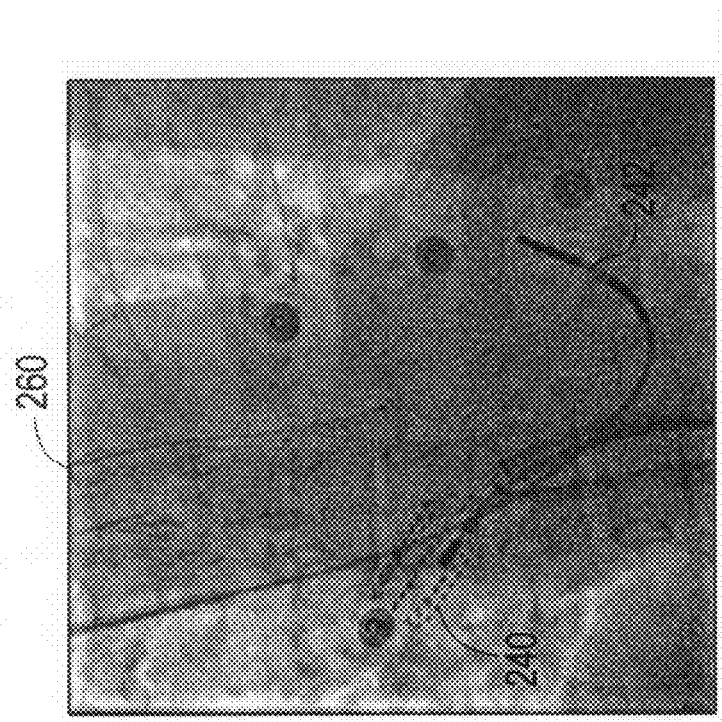
FIG. 12 is a schematic of 2-D image of a catheter in a heart during inspiration by a person.
Figure 11:
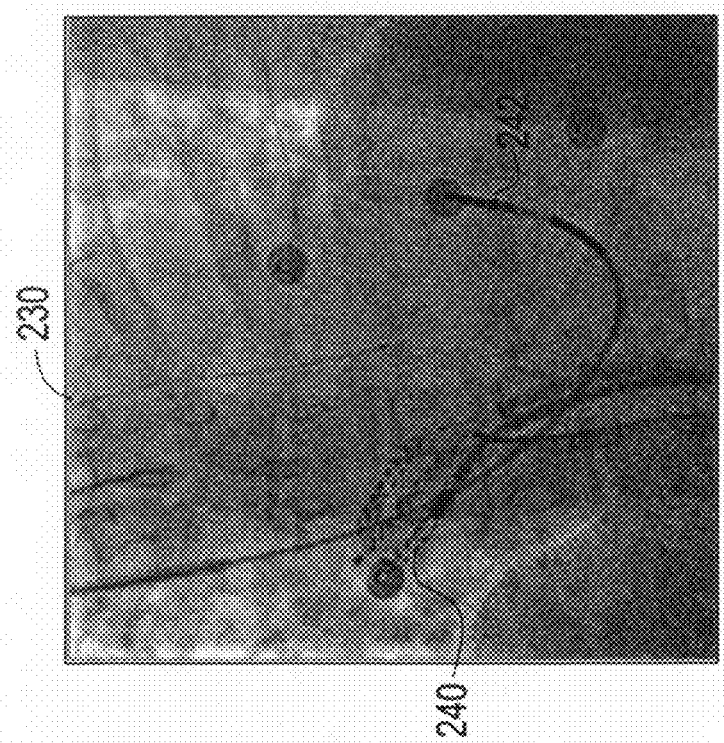
FIG. 11 is a schematic of 2-D image of a catheter in a heart during expiration by a person.

Referring to FIGS. 11 and 12, a brief overview of the methodology utilized by the respiratory monitoring system 28 for determining a phase of a respiratory cycle will now be provided. FIG. 11 corresponds to a 2-D image 230 obtained from the fluoroscopy image acquisition system 24 during an expiration phase of a respiratory cycle. The 2-D image 230 illustrates a coronary sinus catheter 242 and a diaphragm 240 disposed in a heart of a person. As shown, the coronary sinus catheter 242 and the diaphragm 240 are disposed at a maximum upward position indicating an expiration phase of the respiratory cycle of the person. Accordingly, the respiratory monitoring system 28 can utilize the position of the coronary sinus catheter 242 and the diaphragm 240 in the 2-D image 232 to determine that an expiration phase of the respiratory cycle is detected. FIG. 12 corresponds to a 2-D image 260 obtained from the fluoroscopy image acquisition system 24 during an inspiration phase of a respiratory cycle. The 2-D image 230 illustrates the coronary sinus catheter 242 and the diaphragm 240 disposed in a heart of a person. As shown, the coronary sinus catheter 242 and the diaphragm 240 are disposed at a maximum downward position indicating an inspiration phase of the respiratory cycle of the person. Accordingly, the respiratory monitoring system 28 can utilize the position of the coronary sinus catheter 242 and the diaphragm 240 in the 2-D image 260 to determine that an inspiration phase of the respiratory cycle is detected. In an alternative embodiment, other devices or tools in the heart other than the coronary sinus catheter 242 and diaphragm 240 could be utilized to determine a phase of a respiratory cycle. Further, in alternative embodiments, other techniques known to those skilled in the art could be utilized to determine a phase of a respiratory cycle.

Figure 13:
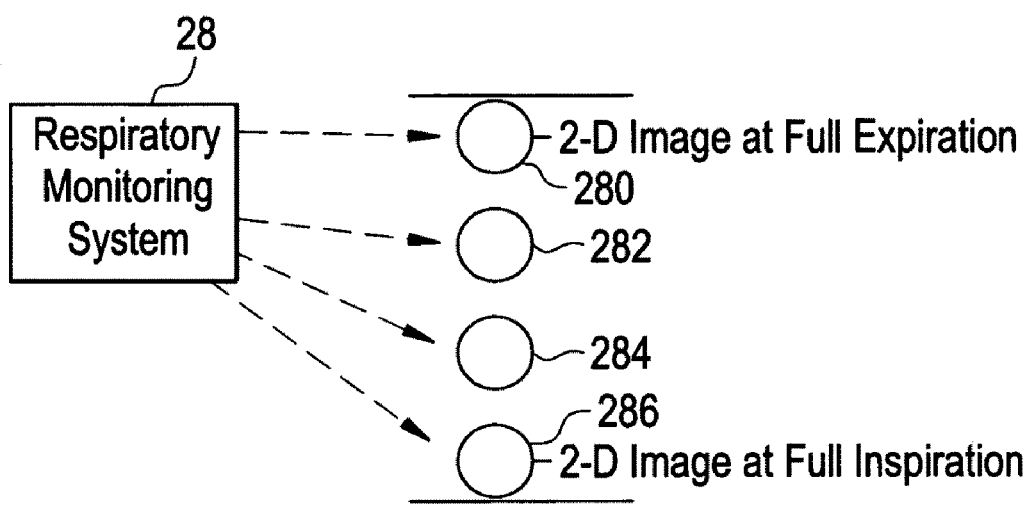
FIG. 13 is a block diagram illustrating a respiratory monitoring system monitoring a phase of a respiratory cycle utilizing 2-D images.

Referring to FIG. 13, during operation in one exemplary embodiment, the respiratory monitoring system 28 receives 2-D images 280, 282, 284, 286 from the fluoroscopy image acquisition system 24 over a respiratory cycle of a person. By detecting a position of catheters in the 2-D images 280, 282, 284, 286, the respiratory monitoring system 28 can determine the phase of a respiratory cycle. Further, the respiratory monitoring system 28 communicates data corresponding to the phase of the respiratory cycle to the registration computer 38.

Another method for obtaining a 2-D image utilizing the fluoroscopy image acquisition system 24 will now be explained. The method includes monitoring cardiac cycles of a person. The method further includes monitoring an operational position of the fluoroscopy paddle 84, utilizing the fluoroscopy image acquisition computer 82. The method further includes generating the 2-D image of an anatomical region of the person when a predetermined phase of the cardiac cycle exists and an operational position of the fluoroscopy paddle 84 is a predetermined operational position, utilizing the fluoroscopy image acquisition computer 82. The method further includes storing the 2-D image in a memory device, utilizing the fluoroscopy image acquisition computer 82.

Referring to FIG. 1, the catheter control system 30 is provided to control operation of the ablation-mapping catheter 32 and to receive signals from the ablation-mapping catheter 32 and the reference catheter 34. During operation, the catheter control system 30 sends control signals to the ablation-mapping catheter 32 to induce the ablation-mapping catheter 32 to perform ablation procedures on the heart.

The ablation-mapping catheter 32 and the reference catheter 34 are also provided to monitor electrical activity in a heart of a person. In particular, the ablation-mapping catheter 32 detects an amplitude of an electrical signal in the heart at a position of the ablation-mapping catheter 32. Further, the ablation-mapping catheter 32 sends a signal to catheter control system 30 indicative of the amplitude of the electrical signal detected by the ablation-mapping catheter 32. The ablation-mapping catheter 32 further includes a position sensor 90 that generates a signal indicative of a position of the catheter 32 in the anatomical region. The reference catheter 34 also detects an amplitude of an electrical signal in the heart at a position of the reference catheter 34. Further, the reference catheter 34 sends a signal to catheter control system 30 indicative of the amplitude of the electrical signal detected by the reference catheter 34.

The catheter position monitoring system 36 is provided to monitor a position of the ablation-mapping catheter 32 with respect to a coordinate system of the catheter position monitoring system 36. In one exemplary embodiment, the catheter position monitoring system 36 generates a fluctuating magnetic field that is detected by the sensor 90 in the ablation-mapping catheter 32. In one exemplary embodiment, the sensor 90 generates a signal responsive to the fluctuating magnetic field that is sent to the catheter control system 30. The catheter control system 30 sends data corresponding to the signal from the sensor 92 the catheter position monitoring system 36. The catheter position monitoring system 36 determines the position of the ablation-mapping catheter 32 with respect to the coordinate system of the system 36, based on the data received from the catheter control system 30. Further, the catheter position monitoring system 36 sends data corresponding to the position of the ablation mapping catheter 32 in the coordinate system of the system 36, to the registration computer 38.

The registration computer 38 is provided to induce the display device 42 to display a location of a point of interest on a 3-D model of an anatomical region, as will be explained in further detail below. The registration computer 38 is further provided to generate a registered image of the anatomical region utilizing the 3-D model of the anatomical region and a 2-D image of the anatomical region, as will be explained in further detail below. The registration computer 38 operably communicates with the fluoroscopy image acquisition computer 82, the CT image acquisition computer 62, the heart monitoring system 26, the catheter control system 30, the catheter position monitoring system 36, the memory device 40, the display device 42, and the input device 44. The input device 44 allows the user to input data utilized by the registration computer 38. In one exemplary embodiment, the input device 44 comprises a computer keyboard. In another exemplary embodiment, the input device 44 comprises a computer mouse. The registration computer 38 is configured to induce the display device to display a graphical user interface for allowing the user to view 2-D images, 3-D models, and registered images. The registration computer 38 is further configured to store data, such as 2-D images, 3-D models, and registered images in the memory device 40.

For purposes of understanding, a general overview of a process for generating a registered image will now be provided. A registered image is generated by combining information from a 2-D image of an anatomical region and a 3-D model of the anatomical region. Registration is the process of aligning images and 3-D models to generate a registered image. Intra-subject multi-modality registration is registration of two different modalities in the same person. The number of parameters needed to describe a transformation (registration) is referred herein as number of "degrees of freedom." Assumption is made that the 3-D model behaves as a rigid body, as the anatomy of the anatomical region being registered has not changed significantly. In this case, three translations and three rotations, which gives six degrees of freedom, will lead to successful registration. Each device used for registration is calibrated to approximate the size of the 3-D model of the anatomical region. This requires three extra degrees of freedom equating to "scaling" in each direction. If a set of corresponding anatomical landmarks (fiducials) x and y can be a defined, then the registration can be affected by selecting a transformation matrix that will align these areas. Each view in the device being used is being referred to as the coordinate system that will define a space in that view. Successful registration involves the determination of a transformation matrix between the individuals in one space (X) of one view, for example with that of another space (Y), for example. Successful registration will involve determination of a transformation matrix T between for the fiducials in the "X" space with those in the "Y" space that minimizes the error (T(x)−y, where T(x)=Ry+t, wherein R is the rotation, and t is the translation.

A transformation matrix defines how to map points from one coordinate system into another coordinate system. By identifying contents of the transformation matrix, several operations including projective transformation, rotation, translation and scaling, between a 2-D image of an anatomical region and a 3-D model of the anatomical region can be performed. In particular, the 2-D image of the anatomical region can be rotated, translated, and scaled (depending if a parallel or conic projection is performed) relative to the 3-D model of the anatomical region. Thereafter, the registered image can be obtained by overlaying the projected, rotated, translated, and scaled 2-D image of the anatomical region on the 3-D model of the anatomical region.

In one exemplary embodiment, instead of aligning an anatomical region in a 2-D image with the anatomical region in a 3-D model, registration is performed by aligning in the 2-D image and the 3-D model, a tool placed by a physician in the anatomical region. For example, a catheter placed in the coronary sinus of a heart can be utilized to align a 2-D image of the heart and a 3-D model of the heart.

A detailed discussion of techniques for obtaining registered images, which can be utilized herein, is discussed in U.S. patent application Ser. No. 10/964,428, entitled "Method And Apparatus For Registering 3D Models of Anatomical Regions Of A Heart And A Tracking System With Projection images Of An Interventional Fluoroscopic System", filed on Oct. 13, 2004, which is incorporated by reference herein; and U.S. patent application Ser. No. 10/964,429, entitled "Method And System For Registering 3D models Of Anatomical Regions With Projection Images Of The Same", filed on Oct. 13, 2004, which is incorporated by reference herein.

Figure 2:
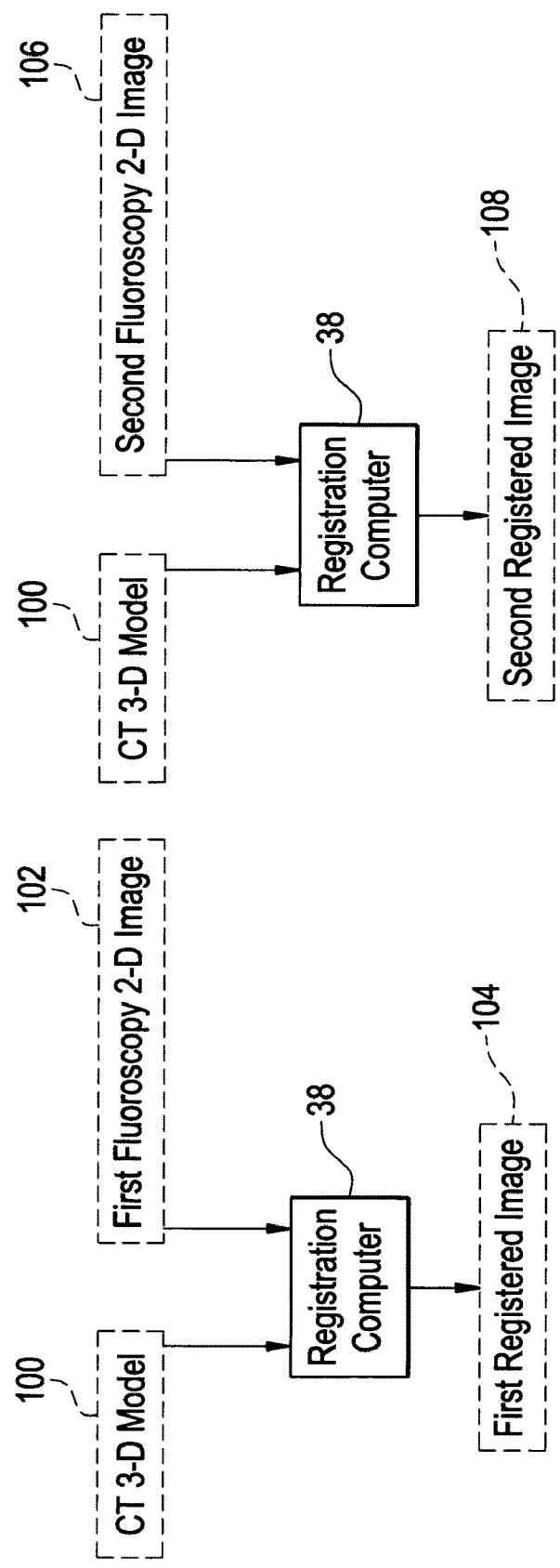
FIG. 2 is a block diagram of a method for generating a registered image.

Referring to FIGS. 1 and 2, a brief explanation of a sequential generation of registered images will be provided. As shown, a 3-D model of an anatomical region, such a 3-D model of a left atrium of a heart for example, is transferred from the CT image acquisition computer 62 to the registration computer 38. When the fluoroscopy paddle 84 is depressed at a first-time, a 2-D image 102 of the anatomical region, such a left atrium of a heart for example, is transferred to the registration computer 38. Thereafter, the registration computer 38 generates a registered image 104 based upon the 3-D model 100 and the 2-D image 102. When the fluoroscopy paddle 84 is depressed at a second time, a 2-D image 106 of the anatomical region such a left atrium of a heart for example, is transferred to the registration computer 38. Thereafter, the registration computer 38 generates a registered image 108 based upon the 3-D model 100 and the 2-D image 106.

Figure 3:
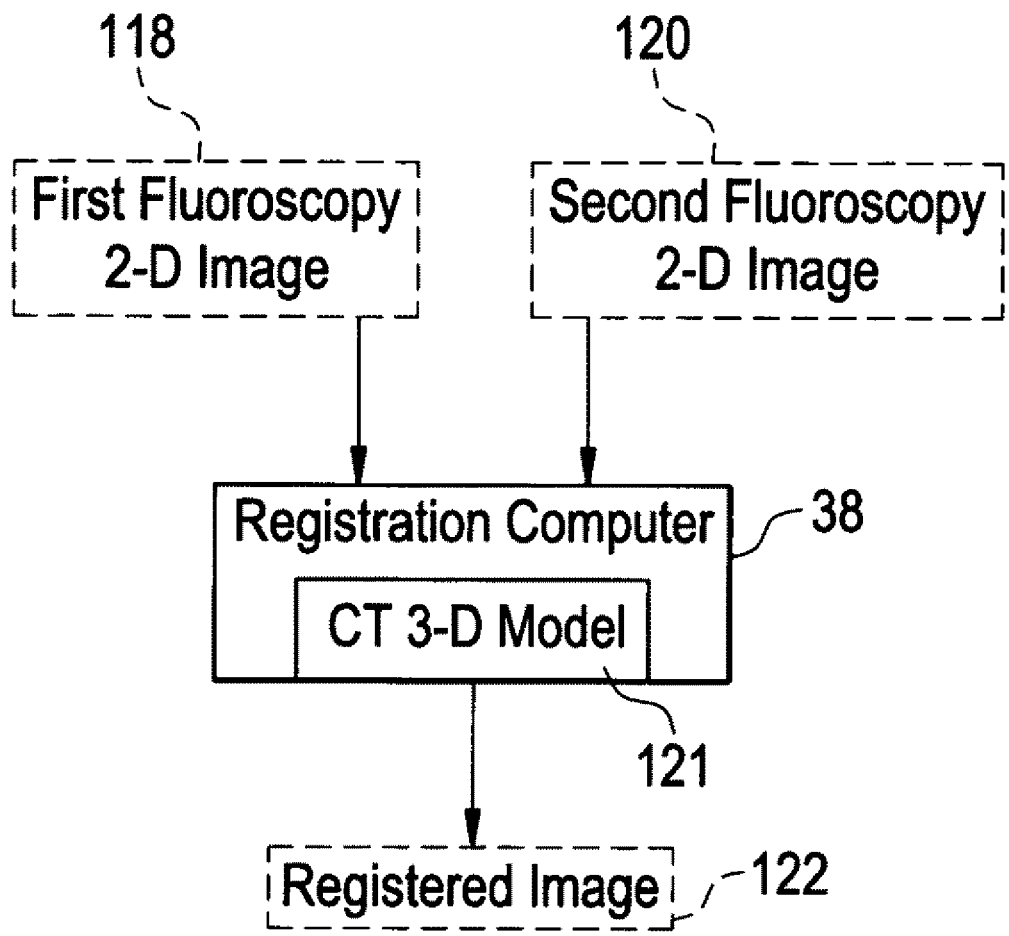
FIG. 3 is a block diagram of another method for generating a registered image.
Figure 4:
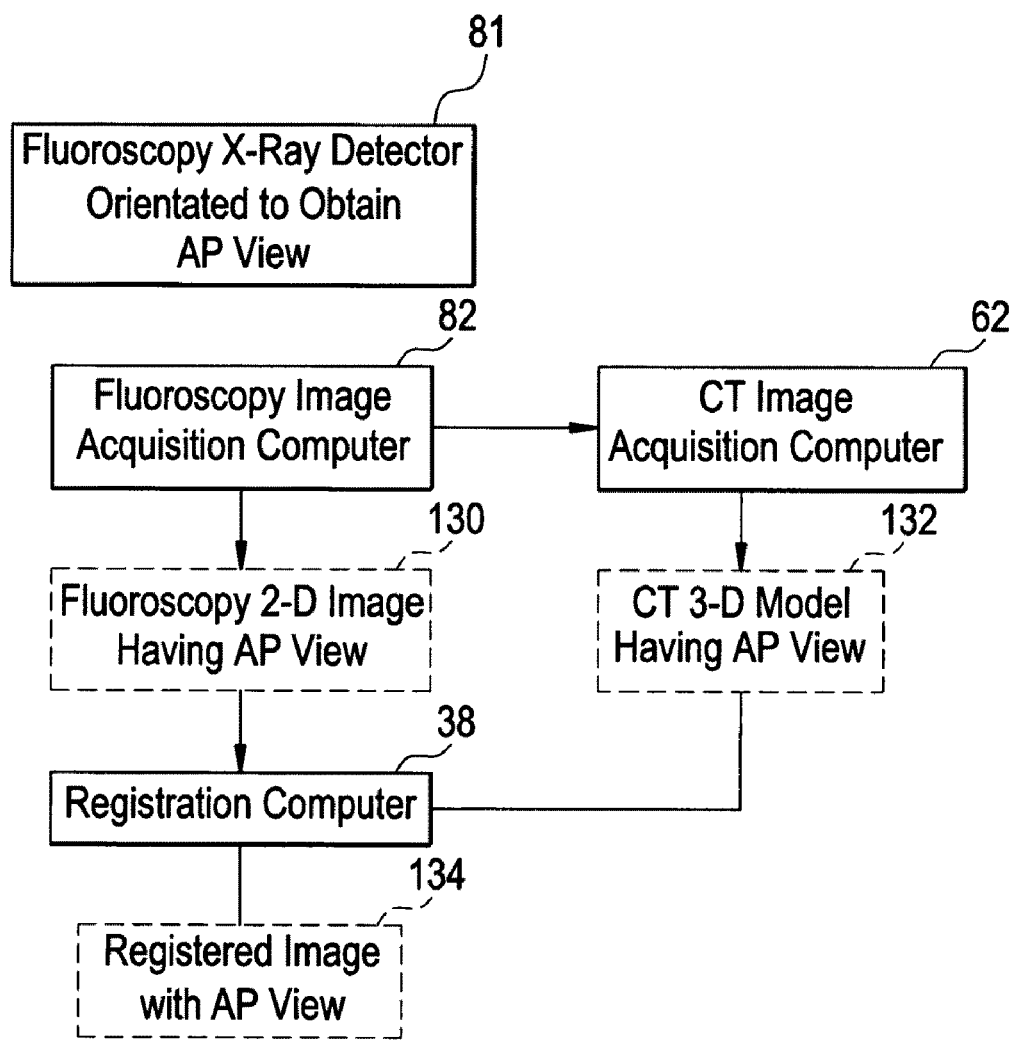
FIG. 4 is a block diagram of a method for generating a registered image utilizing a 2-D image and a 3-D model having similar orientations.
Figure 5:
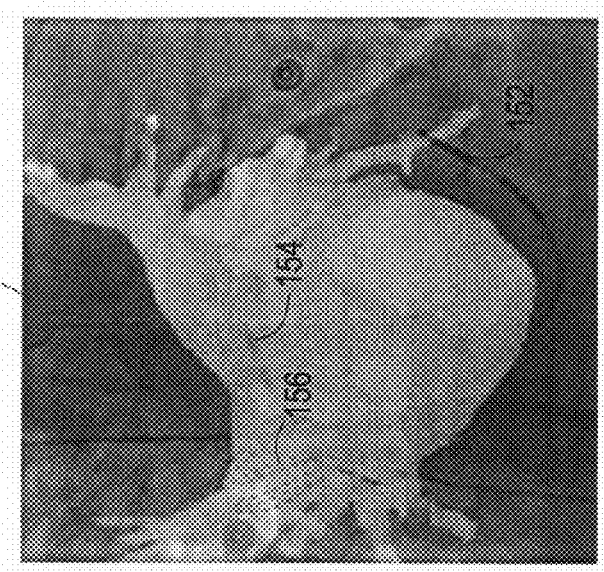
FIG. 5 is a schematic of a 2-D image having an anteroposterior view of a heart.
Figure 6:
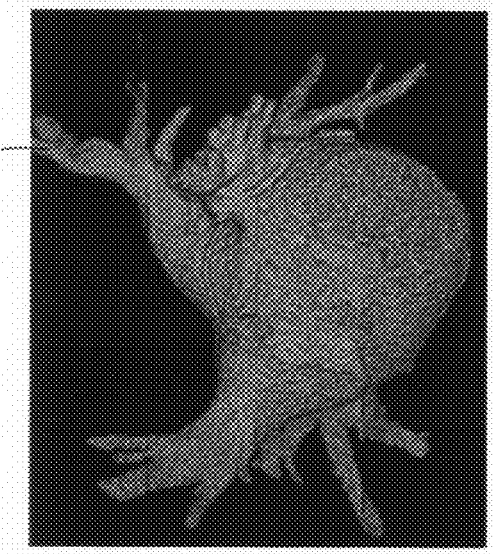
FIG. 6 is a schematic of a 3-D model of a heart.
Figure 7:
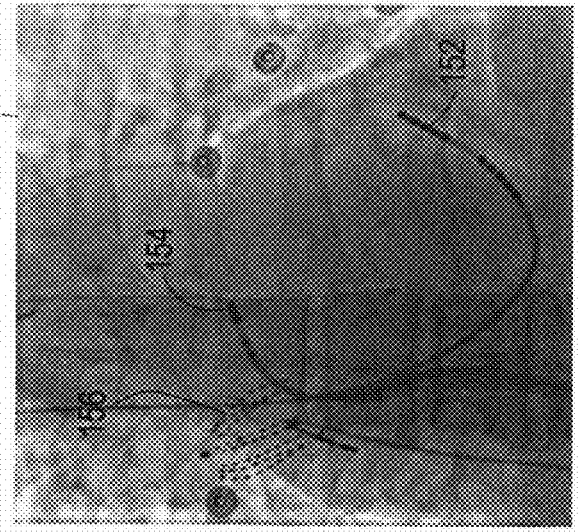
FIG. 7 is a schematic of a registered image generated from the 2-D image of FIG. 5 and the 3-D model of FIG. 6.

Referring to FIG. 3, a brief explanation of another technique for sequentially generating registered images will be provided. As shown, a 3-D model 121 is stored in the registration computer 38. When the fluoroscopy paddle 84 is depressed at a first time, a 2-D image 118 of the anatomical region such a left atrium of a heart for example, is transferred to the registration computer 38. Thereafter, the registration computer 38 generates a registered image 122 based upon the 3-D model 121 and the 2-D image 11 8. When the fluoroscopy paddle 84 is depressed at a second time, a 2-D image 120 of the anatomical region such a left atrium of a heart for example, is transferred to the registration computer 38. Thereafter, the registration computer 38 generates another registered image based upon the 3-D model 121 and the 2-D image 120.

Referring to FIGS. 4-7, a technique for obtaining a similar orientation of 2-D image of an anatomical region and a 3-D image of anatomical region will be explained. In this example, the anatomical region is a human heart. As shown, a fluoroscopy X-ray detector 81 is orientated to obtain an antero-posterior (AP) orientation of the heart. The fluoroscopy image acquisition computer 82 generates a 2-D image 130 of the heart having an AP orientation and sends the 2-D image 132 to the registration computer 38. The fluoroscopy image acquisition computer 82 further sends data to the CT image acquisition computer 62 indicating an AP orientation is desired. The CT image acquisition computer 62 generates a 3-D model 132 of the heart having an AP orientation and sends the 3-D model 132 to the registration computer 38. Thus, the registration computer 38 receives a 2-D image and a 3-D model having a similar orientation. Thereafter, the registration computer 38 generates a registered image 134 with an AP orientation based on the 2-D image 130 and the 3-D model 132. As shown, the 2-D image 130 illustrates an antero-posterior orientation of the heart having a sinus catheter 152, and ablation mapping catheter 154, and a multi-electrode basket catheter 156. Further, the registered image illustrates an antero-posterior orientation of the heart including the sinus catheter 152, the ablation mapping catheter 154 and the multi electrode basket catheter 156.

Referring to FIG. 8, a brief description of a technique for obtaining a registered image of an anatomical region having a predetermined phase of a cardiac cycle and a predetermined phase of a respiration cycle will be described. As shown, the fluoroscopy image acquisition computer 82 generates: (i) a 2-D image 200 at a 25% phase of a cardiac cycle and a full expiration phase of a respiratory cycle, (ii) a 2-D image 202 at a 50% phase of the cardiac cycle and the full expiration phase of the respiratory cycle, (iii) a 2-D image 204 at a 75% phase of the cardiac cycle and the full expiration phase of the respiratory cycle, and (iv) a 2-D image 206 at a 100% phase of the cardiac cycle and the full expiration phase of the respiration cycle. Thereafter, the registration computer 38 selects the 2-D image 204 at a 75% phase of the cardiac cycle and the full expiration phase of the respiratory cycle, corresponding to the 3-D model 208 having a 75% phase of the cardiac cycle and the full expiration phase of the respiratory cycle. Thereafter, the registration computer 38 generates a registered image 210 based on the 2-D image 204 and the 3-D model 208.

Figure 14:
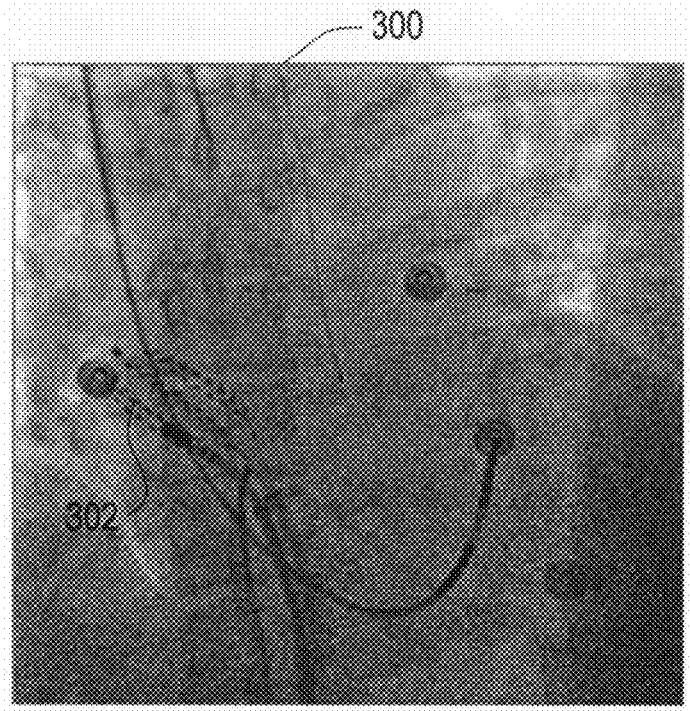
FIG. 14 is a schematic of a 2-D image of a heart obtained at a predetermined phase of the cardiac cycle in a predetermined phase of a respiratory cycle.
Figure 15:
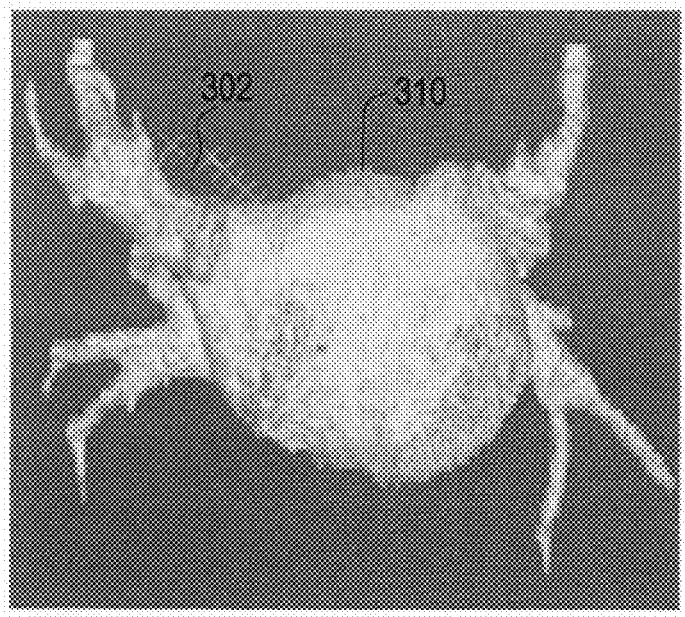
FIG. 15 is a schematic of a registered image of the heart generated by the 2-D image of FIG. 14 and a 3-D model.

Referring to FIGS. 14 and 15, a 2-D image 300 of a heart and a 3-D model 310 of the heart is illustrated. The 2-D image 300 and a 3-D model of the heart having a similar phase of a cardiac cycle and a similar phase of a respiratory cycle were utilized to generate the registered image 3 10. As shown, both the 2-D image 300 and the registered image 310 illustrate a multi-electrode basket catheter 302 in the heart.

Referring to FIG. 16, a flowchart of a method for generating a registered image utilizing cardiac gating and respiratory gating will now be explained.

At step 320, the heart monitoring system 26 monitors cardiac cycles of a person.

At step 322, the respiratory monitoring system monitors respiratory cycles of the person.

At step 324, the fluoroscopy image acquisition system 24 generates a plurality of 2-D images of an anatomical region of the person.

At step 326, the CT image acquisition system 22 generates a 3-D model of the anatomical region of the person. The 3-D model is associated with a predetermined phase of a cardiac cycle and a predetermined phase of a respiratory cycle.

At step 328, the computer 38 selects a first 2-D image from the plurality of 2-D images associated with the predetermined phase of the cardiac cycle and the predetermined phase of the respiratory cycle. The computer 38 operably communicates with the heart monitoring system 26, the respiratory monitoring system 28, the fluoroscopy image acquisition system 24, and the CT image acquisition system 22.

At step 330, the computer 38 generates a registered image utilizing the first 2-D image and the 3-D model.

At step 332, the computer 38 induces the display device 42 to display the registered image.

At step 334, the computer 38 stores the registered image in the memory device 40.

Figure 19:
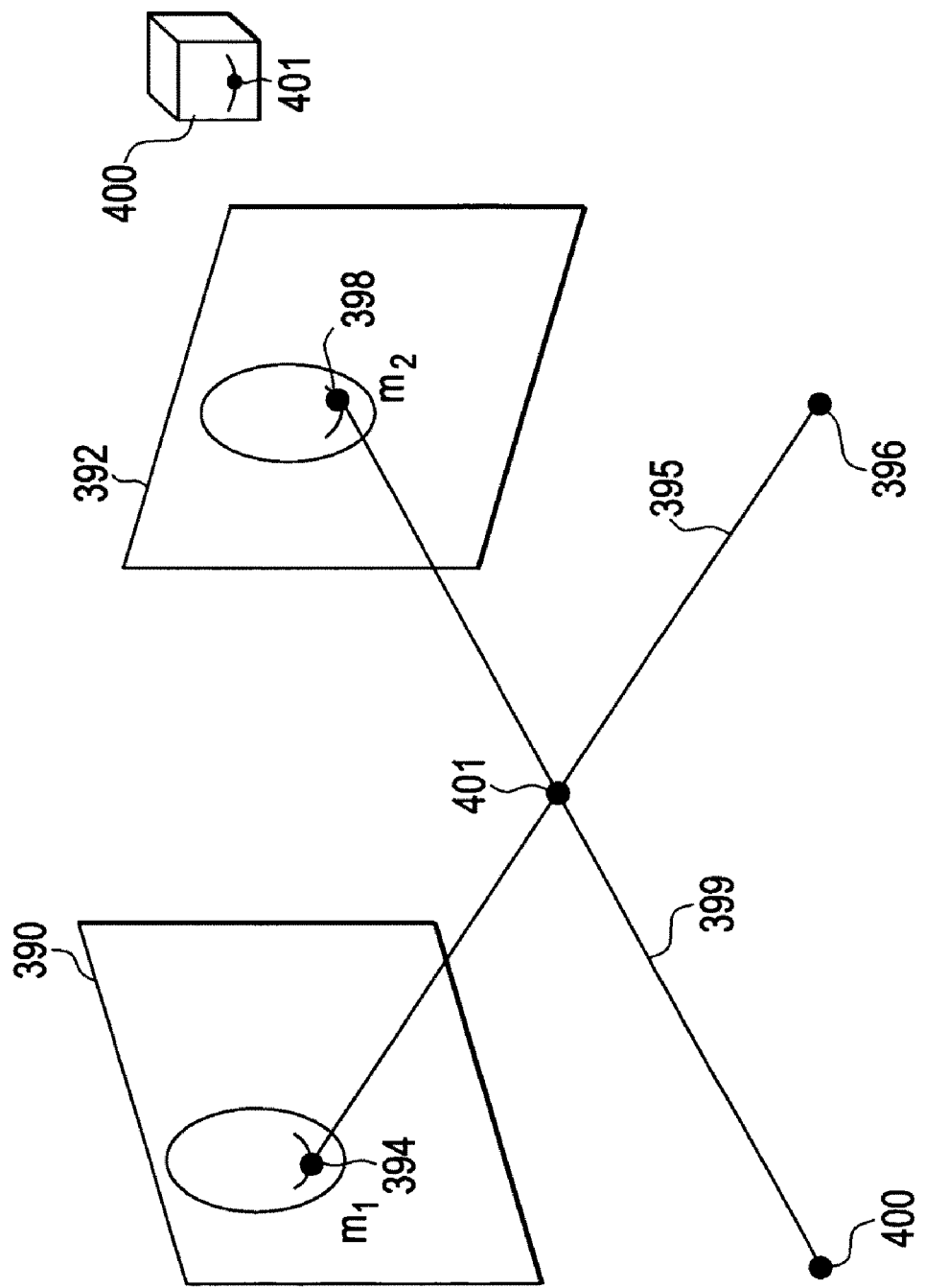
FIG. 19 is a schematic of exemplary 2-images and a 3-model utilized in the method of FIGS. 17-18.
Figure 20:
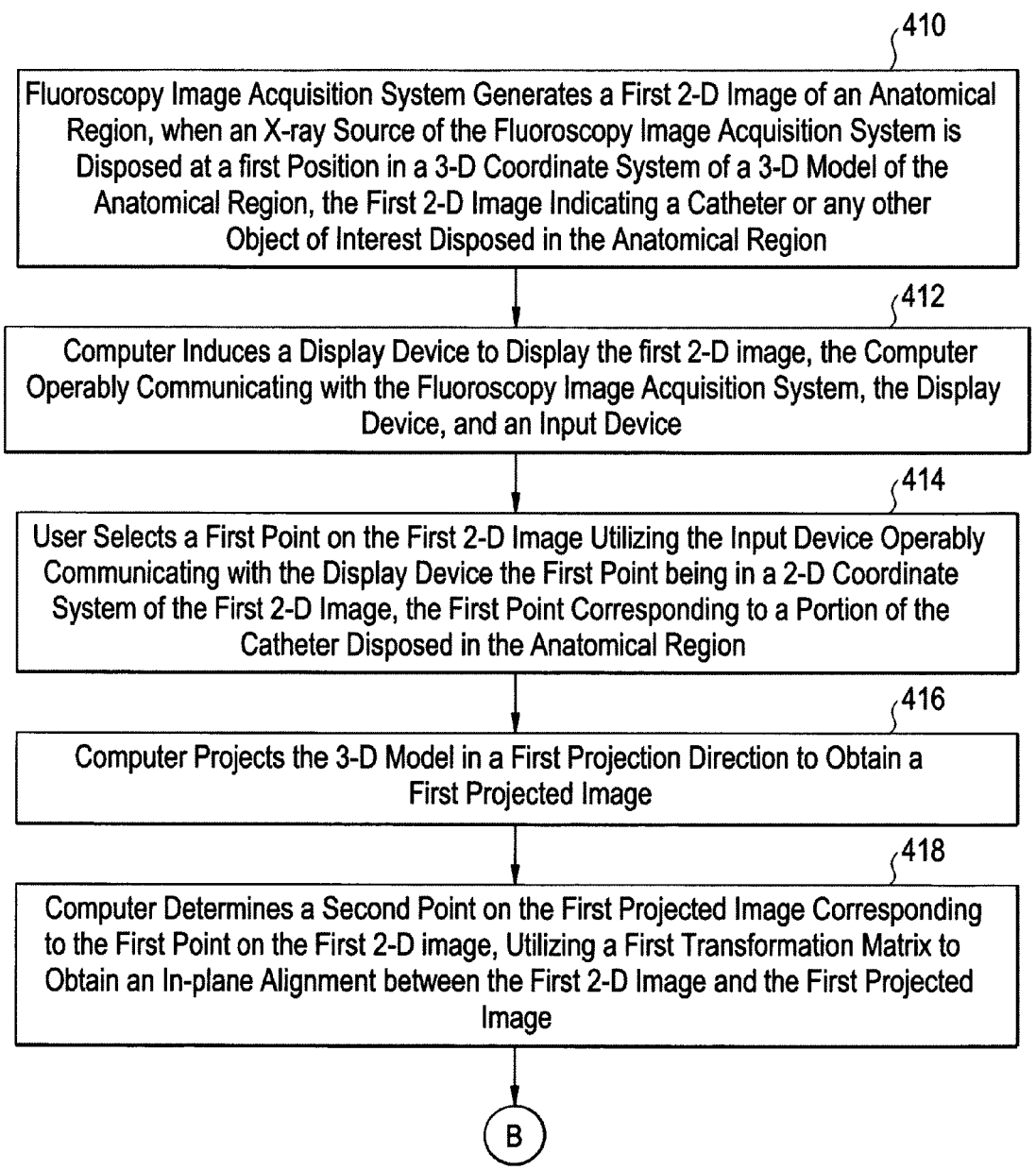
FIGS. 20-22 are flowcharts of a method for displaying a location of a point of interest on a 3-D model of an anatomical region of a person in accordance with another exemplary embodiment.
Figure 21:
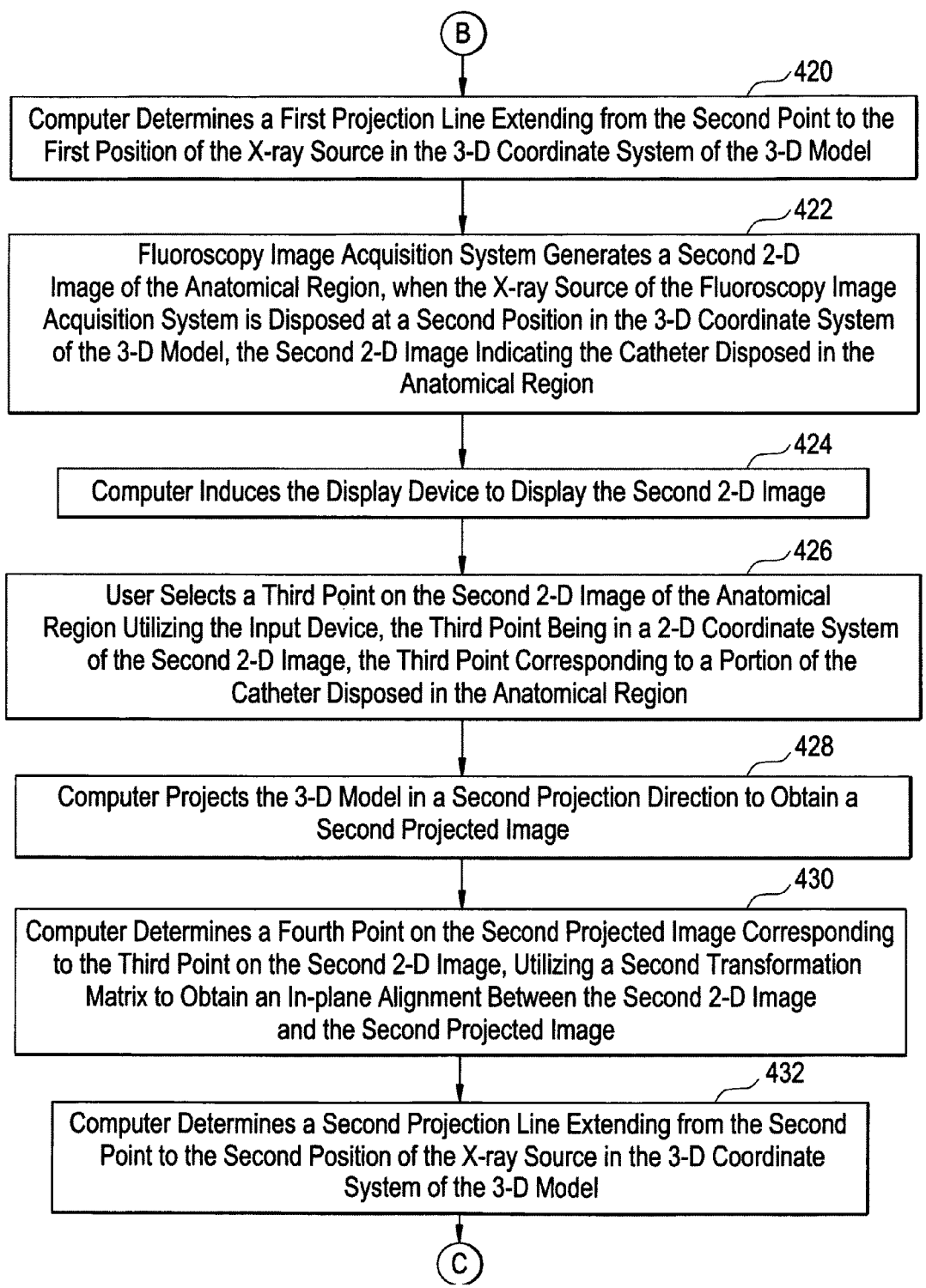
Figure 17:
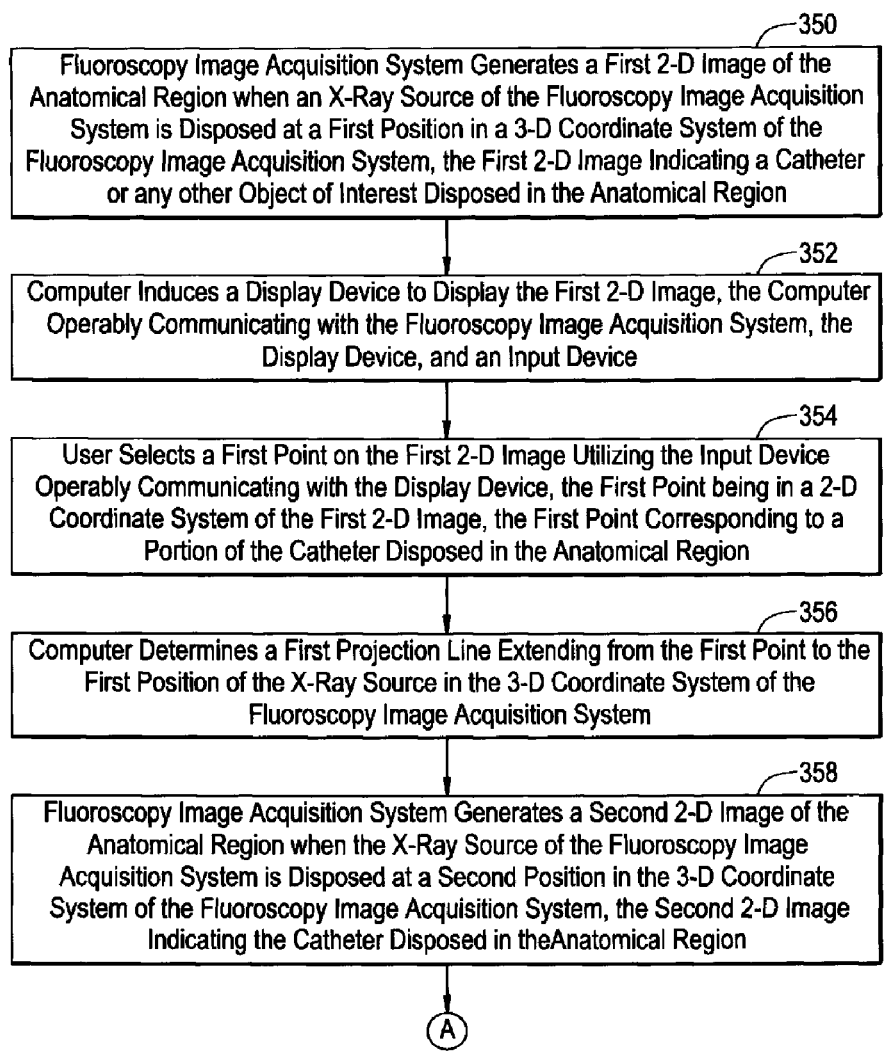
Figure 35:
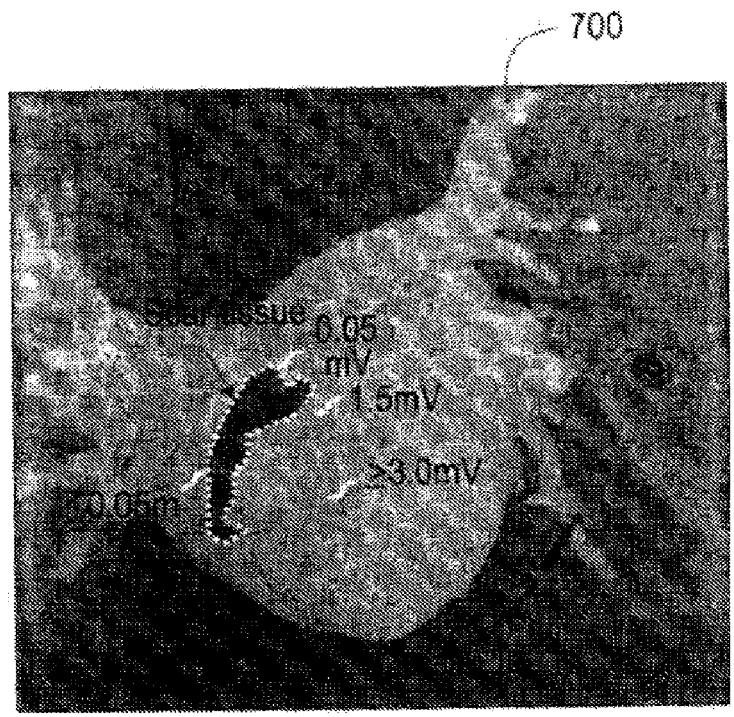
Figure 35:
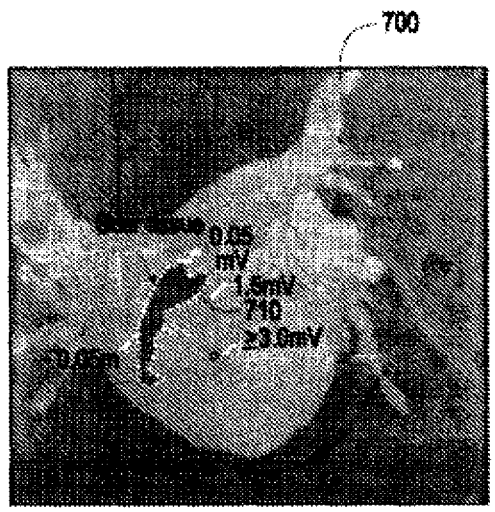

Referring to FIGS. 17-19, a flowchart of a method for displaying a location of a point of interest on a 3-D model of anatomical region of a person in accordance with an exemplary embodiment will now be explained.

At step 350, the fluoroscopy image acquisition system 24 generates a first 2-D image 390 of the anatomical region when the X-ray source 80 of the fluoroscopy image acquisition system 24 is disposed at a first position 396 in a 3-D coordinate system of the fluoroscopy image acquisition system 24. The first 2-D image 390 indicates a catheter or any other object of interest disposed in the anatomical region.

At step 352, that computer 38 induces the display device 42 to display the first 2-D image 390. The computer 38 operably communicates with the fluoroscopy image acquisition system 24, the display device 42, and the input device 44.

At step 354, a user selects a first point 394 on the first 2-D image 390 utilizing the input device 44 operably communicating with the display device 42. The first point 394 is in a 2-D coordinate system of the first 2-D image 390. The first point 394 corresponds to a portion of the catheter disposed in the anatomical region.

At step 356, the computer 38 determines a first projection line 395 extending from the first point 394 to the first position 396 of the X-ray source 80 in the 3-D coordinate system of the fluoroscopy image acquisition system 24.

At step 358, the fluoroscopy image acquisition system 24 generates a second 2-D image 392 of the anatomical region when the X-ray source 80 of the fluoroscopy image acquisition system 24 is disposed at a second position 400 in the 3-D coordinate system of the fluoroscopy image acquisition system 24. The second 2-D image 392 indicates the catheter disposed in the anatomical region.

At step 360, the computer 38 induces the display device 42 to display the second 2-D image 392.

At step 362, a user selects a second point 398 on the second 2-D image 392 utilizing the input device 44. The second point 398 is in a 2-D coordinate system of the second 2-D image 398. The second point 398 corresponds to a portion of the catheter disposed in the anatomical region.

At step 364, the computer 38 determines a second projection line 399 extending from the second point 398 to the second position 400 of the X-ray source 80 in the 3-D coordinate system of the fluoroscopy image acquisition system 24.

At step 366, the computer 38 determines the point of interest 401 in the coordinate system of the fluoroscopy image acquisition system 24 that corresponds to an intersection point of the first and second projection lines 395, 399.

At step 368, the computer 38 determines a position of the point of interest 401 in a 3-D coordinate system of a 3-D model 400 of the anatomical region, utilizing a transformation matrix. Two projective equations that have two transformation matrices utilized to calculate the position of the point of interest 401 are as follows:

$$\begin{pmatrix} su_1 \\ sv_1 \\ s \end{pmatrix} = P_1 \begin{pmatrix} X \\ Y \\ Z \\ 1 \end{pmatrix} \text{ and } \begin{pmatrix} su_2 \\ sv_2 \\ s \end{pmatrix} = P_2 \begin{pmatrix} X \\ Y \\ Z \\ 1 \end{pmatrix}$$

In the first equation, the terms $u_1$, $v_1$ correspond to the u, v coordinates of the point 394 in the coordinate system of the 2-D image 390. The terms X, Y, Z in the first equation correspond to the point of interest 401 in the coordinate system of the 3-D model 400. The term $P_1$ corresponds to a transformation matrix to transform the coordinates in the 2-D image 390 to the coordinate system of the 3-D model 400. In the second equation, the terms $u_2$, $v_2$ correspond to the u, v coordinates of the point 398 in the 2-D image 392. The terms X, Y, Z in the second equation correspond to the point of interest 401 in the coordinate system of the 3-D model 400. The term $P_2$ corresponds to a transformation matrix to transform the coordinates in the 2-D image 392 to the coordinate system of the 3-D model 400. By solving these two equations, the coordinates X, Y, Z of the point of interest 401 in the coordinate system of the 3-D model 400 can be determined.

At step 370, the computer 38 attaches a marking icon at the point of interest 401 in the 3-D model 400 of the anatomical region.

At step 372, the computer 38 induces the display device 42 to display the 3-D model 400 of the anatomical region having the marking icon indicating the position of the point of interest 401.

At step 374, the computer 38 stores the 3-D model 400 with the marking icon in the memory device 40.

Referring to FIGS. 20-23, a flowchart of a method for displaying a location of a point of interest on a 3-D model of anatomical region of a person in accordance with another exemplary embodiment will now be explained.

At step 410, the fluoroscopy image acquisition system 24 generates a first 2-D image 450 of an anatomical region, when the X-ray source 80 of the fluoroscopy image acquisition system 24 is disposed at a first position 460 in a 3-D coordinate system of a 3-D model 454 of the anatomical region. The first 2-D image 450 indicates a catheter or any other object of interest disposed in the anatomical region.

At step 412, the computer 38 induces the display device 42 to display the first 2-D image 450. The computer 38 operably communicates with the fluoroscopy image acquisition system 24, the display device 42, and the input device 44.

At step 414, a user selects a first point 452 on the first 2-D image 450 utilizing the input device 44 operably communicating with the display device 42. The first point 452 is in a 2-D coordinate system of the first 2-D image 450. The first point 452 corresponds to a portion of the catheter disposed in the anatomical region.

At step 416, the computer 38 projects the 3-D model 454 in a first projection direction to obtain a first projected image 456.

At step 418, the computer 38 determines a second point 458 on the first projected image 456 corresponding to the first point 452 on the first 2-D image 450, utilizing a first transformation matrix to obtain an in-plane alignment between the first 2-D image 450 and the first projected image 456.

At step 420, the computer 38 determines a first projection line 462 extending from the second point 458 to the first position 460 of the X-ray source 80 in the 3-D coordinate system of the 3-D model 454.

At step 422, the fluoroscopy image acquisition system 24 generates a second 2-D image 470 of the anatomical region, when the X-ray source 80 of the fluoroscopy image acquisition system 24 is disposed at a second position 478 in the 3-D coordinate system of the 3-D model 454. The second 2-D image 470 indicates the catheter disposed in the anatomical region.

At step 424, the computer 38 induces the display device 42 to display the second 2-D image 470.

At step 426, a user selects a third point 472 on the second 2-D image 470 of the anatomical region utilizing the input device 44. The third point 472 is in a 2-D coordinate system of the second 2-D image 470. The third point 472 corresponds to a portion of the catheter disposed in the anatomical region.

At step 428, the computer 38 projects the 3-D model 454 in a second projection direction to obtain a second projected image 474.

At step 430, the computer 38 determines a fourth point 476 on the second projected image 474 corresponding to the third point 472 on the second 2-D image 470, utilizing a second transformation matrix to obtain an in-plane alignment between the second 2-D image 470 and the second projected image 474.

At step 432, the computer 38 determines a second projection line 480 extending from the second point 476 to the second position 478 of the X-ray source 80 in the 3-D coordinate system of the 3-D model 454.

At step 434, the computer 38 determines the point of interest 482 in the 3-D coordinate system of the 3-D model 454 that corresponds to an intersection point of the first and second projection lines 462, 480.

At step 436, the computer 38 attaches a marking icon at the point of interest 482 in the 3-D model 454 of the anatomical region.

At step 438, the computer 38 induces the display device 42 to display the 3-D model 454 of the anatomical region having the marking icon at the position of the point of interest 482.

At step 440, the computer 38 stores the 3-D model 454 with the marking icon in the memory device 40.

Figure 24:
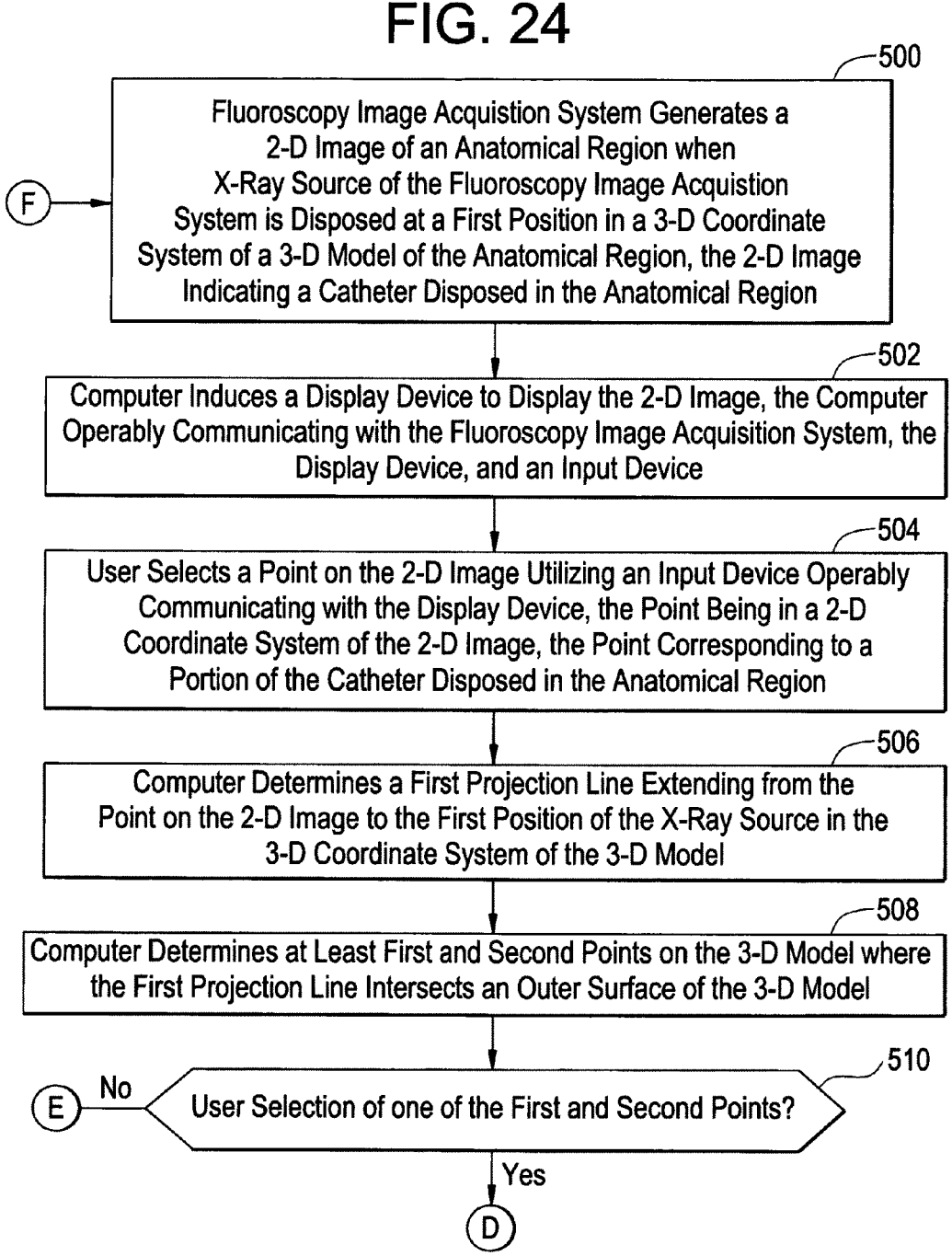
FIGS. 24-25 are flowcharts of a method for displaying a location of a point of interest on a 3-D model of an anatomical region of a person in accordance with another exemplary embodiment.
Figure 25:
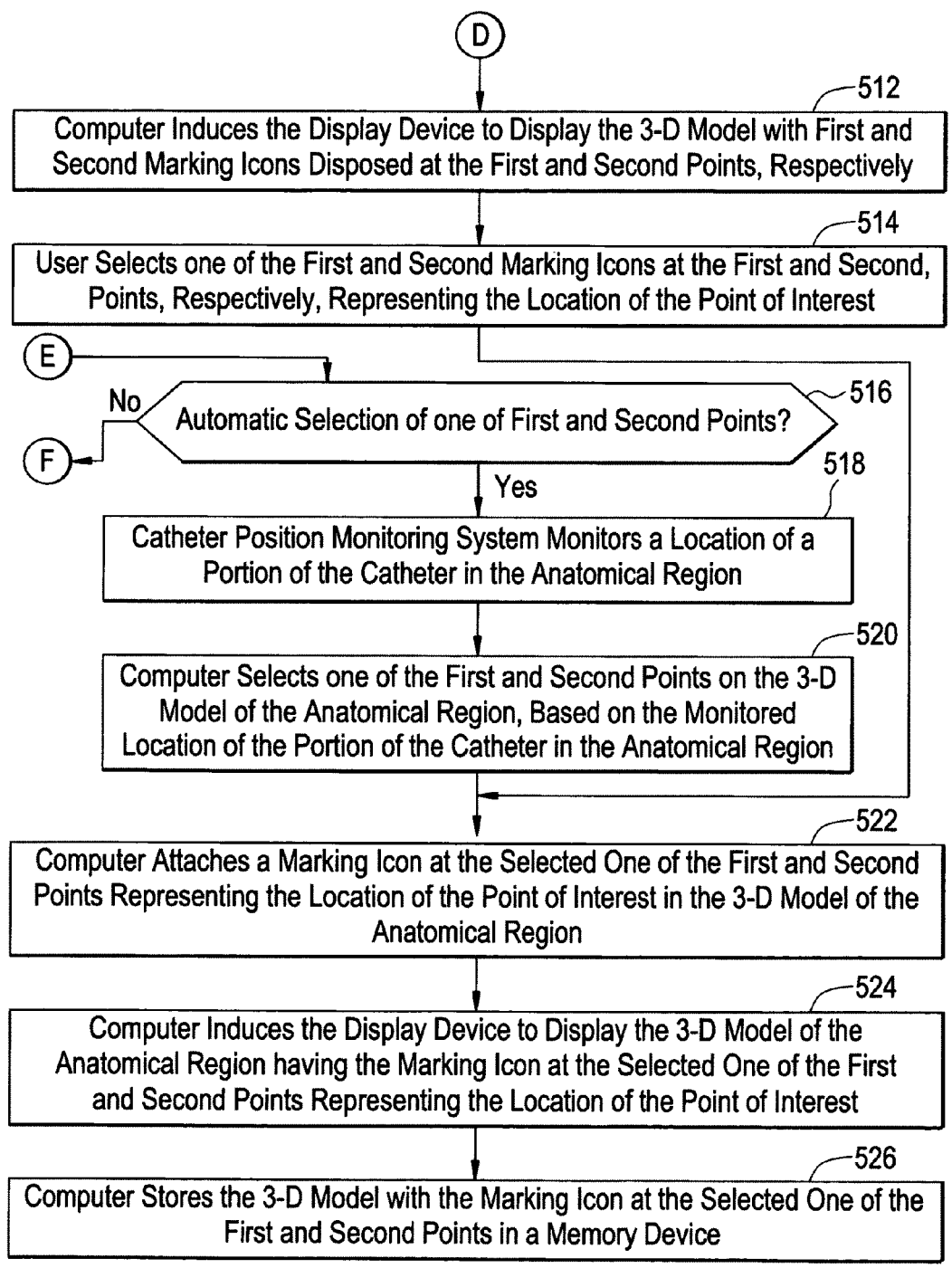
Figure 26:
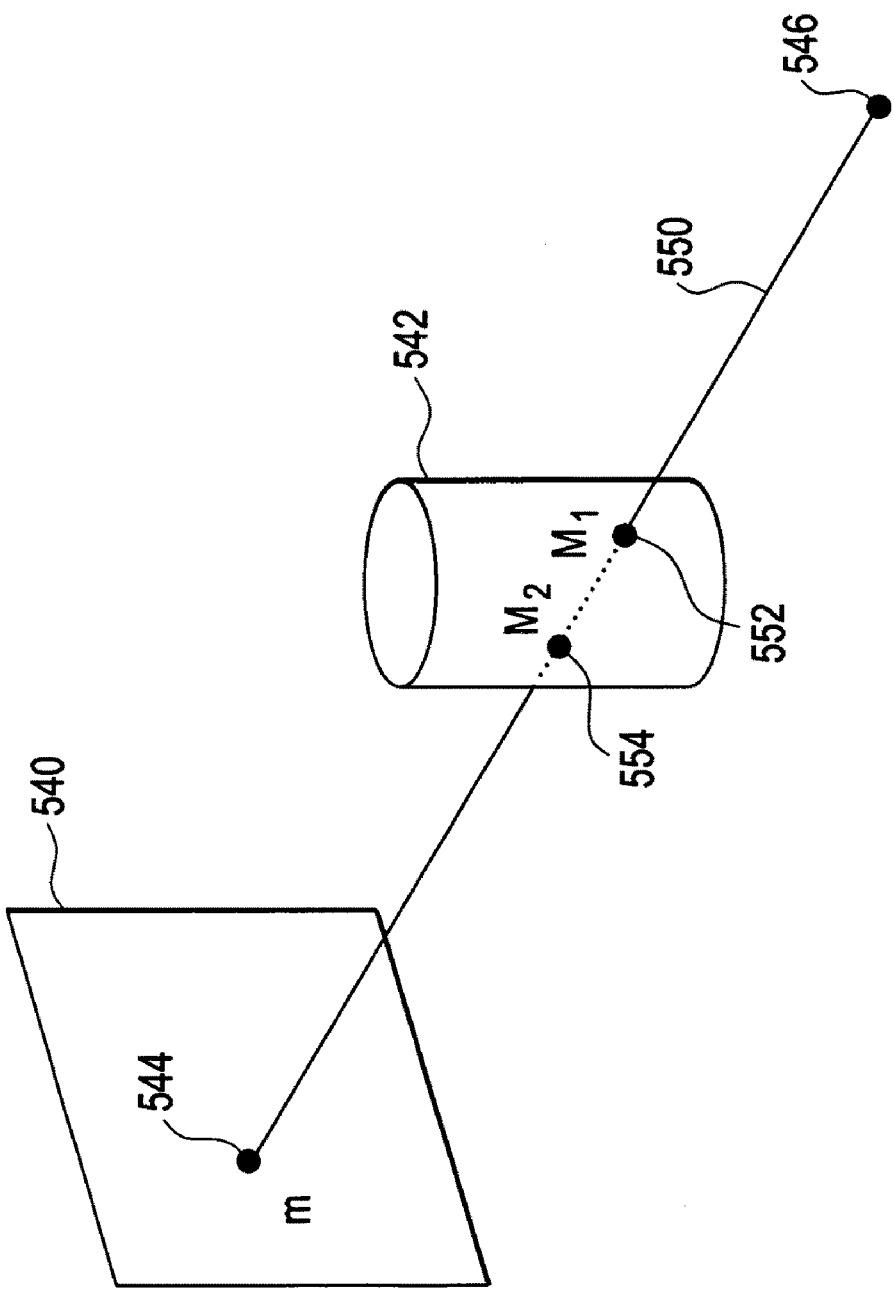
FIG. 26 is a schematic of an exemplary 2-image and a 3-model utilized in the method of FIGS. 24-25.
Figure 27:
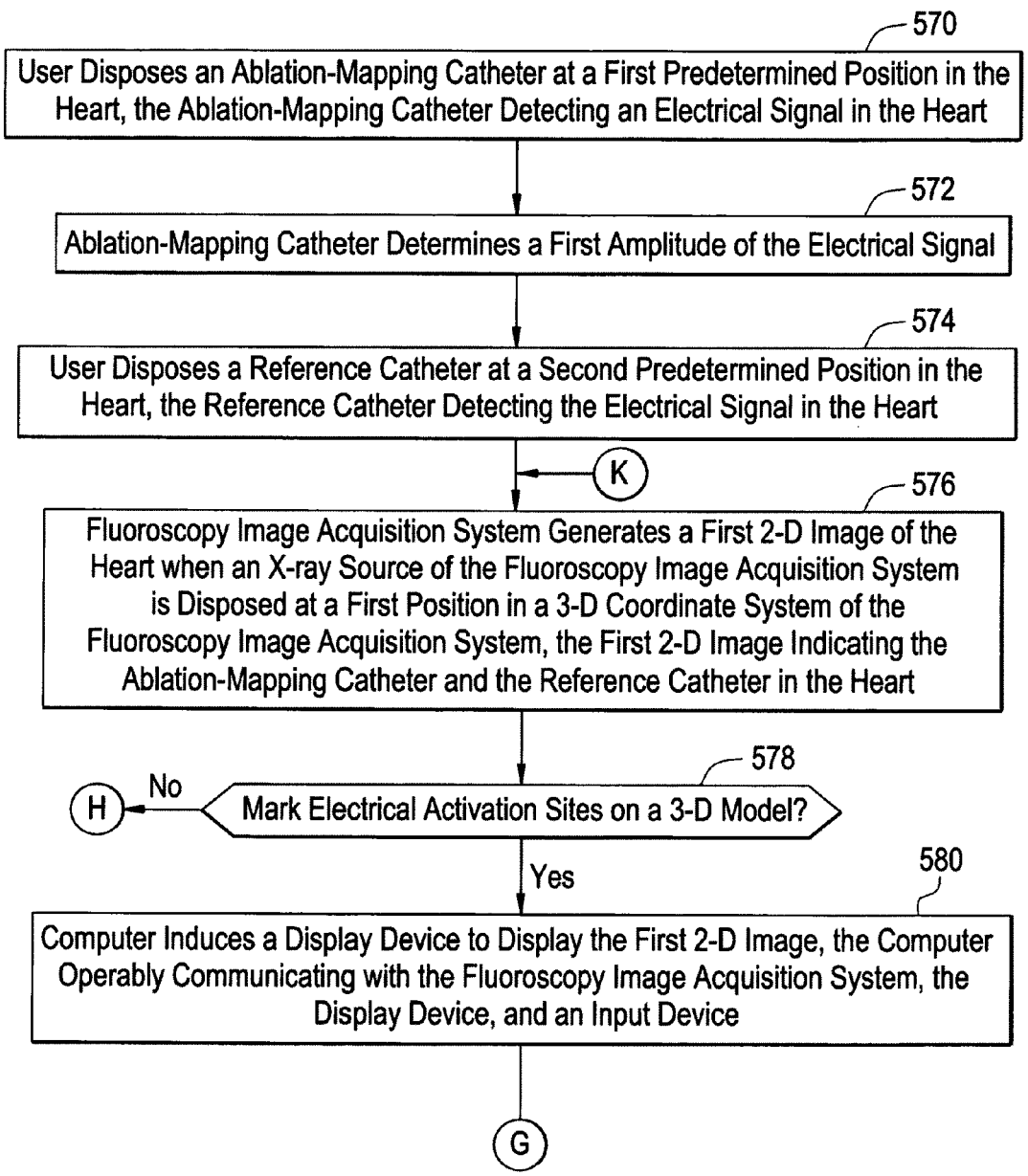
Figure 28:
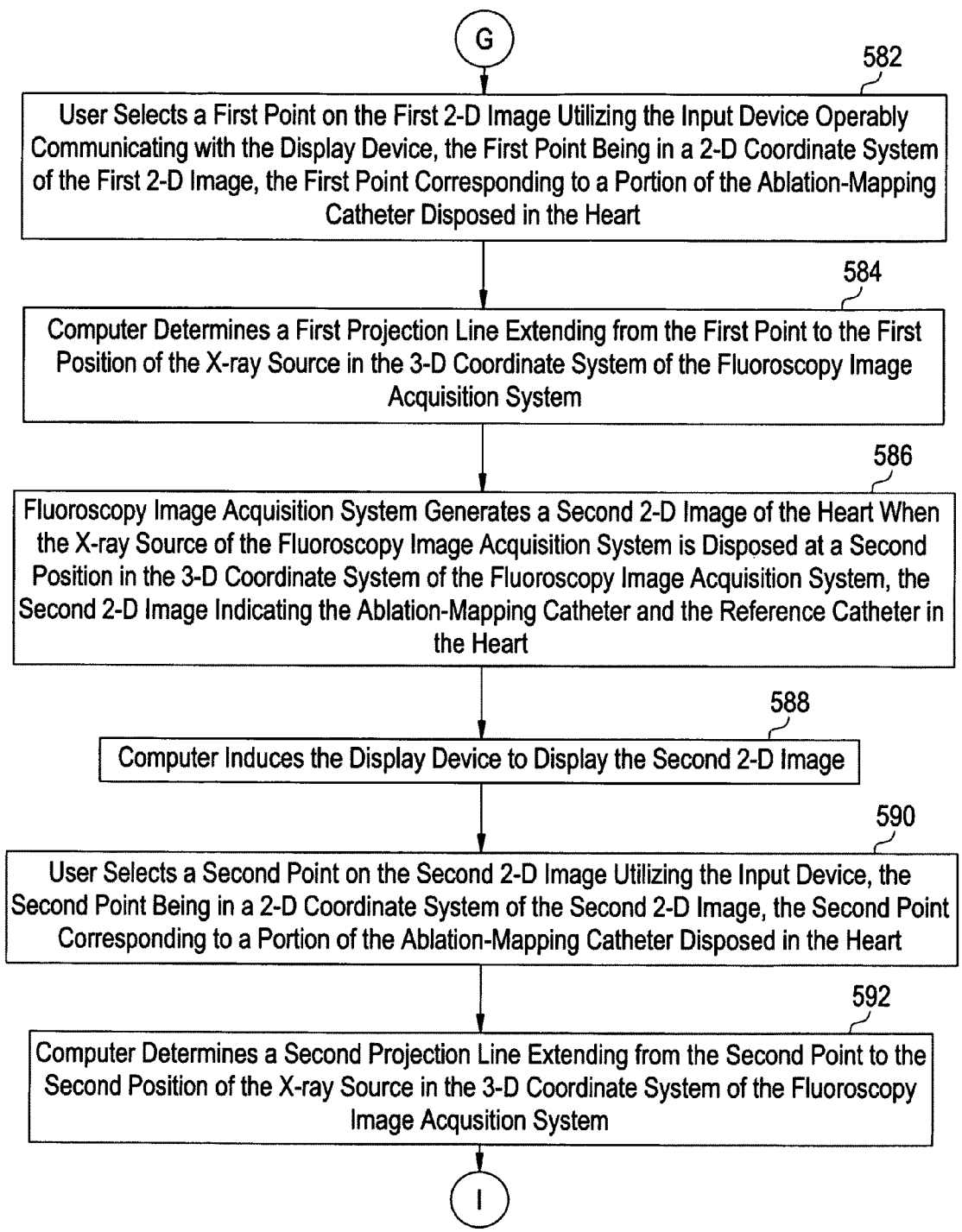
Figure 29:
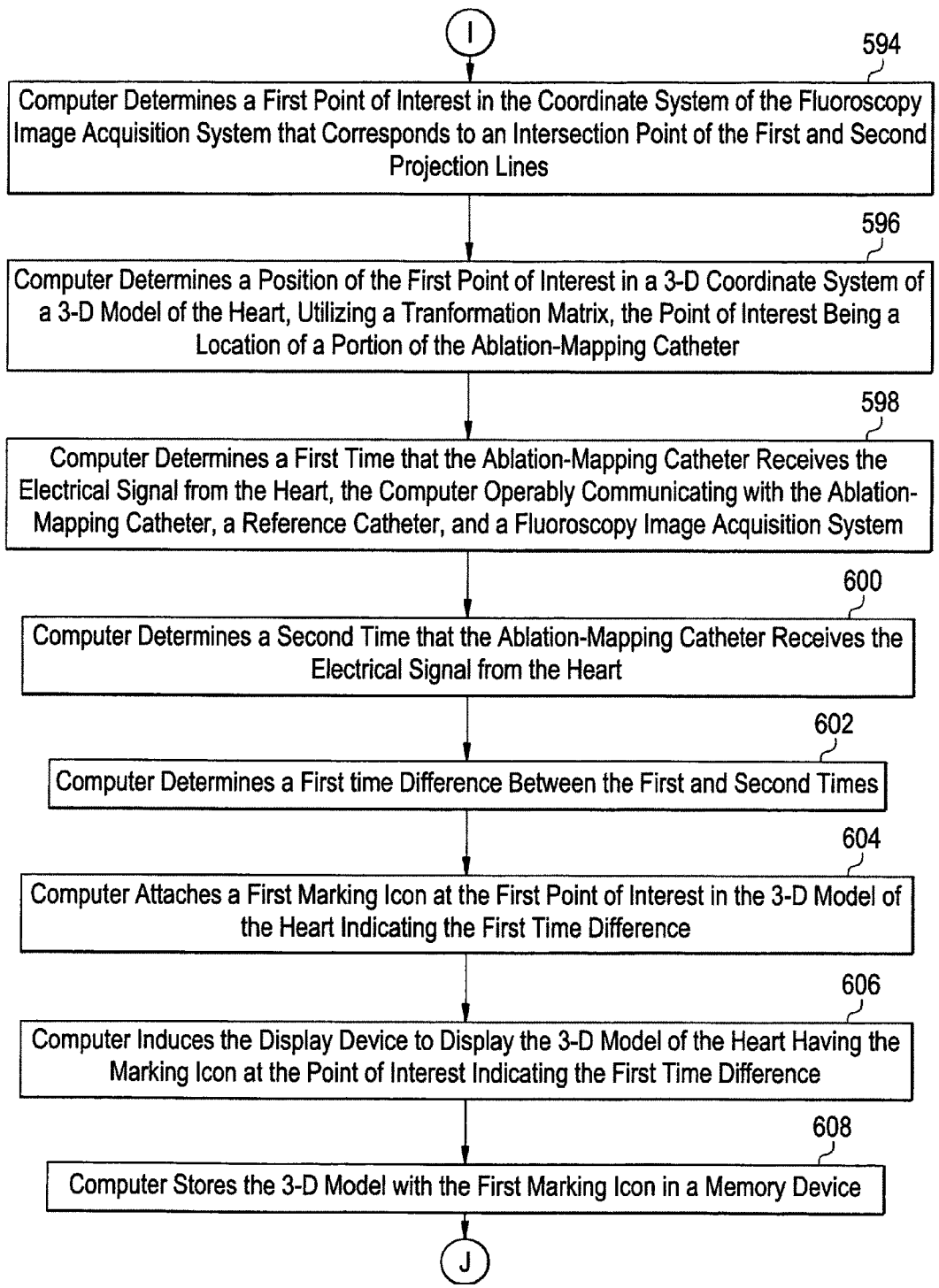
Figure 30:
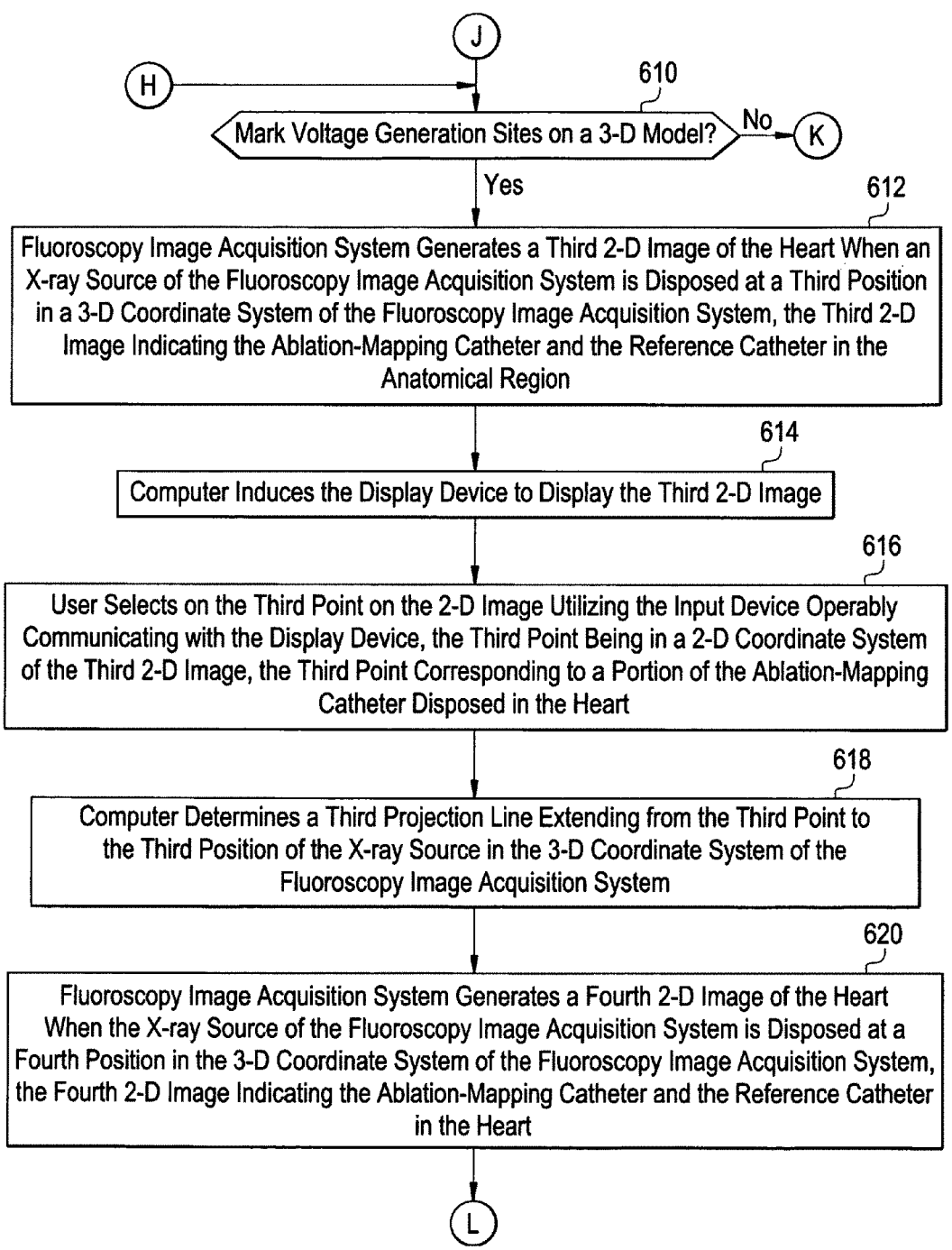

Referring to FIGS. 24-26, a flowchart of a method for displaying a location of a point of interest on a 3-D model of anatomical region of a person in accordance with another exemplary embodiment will now be explained.

At step 500, the fluoroscopy image acquisition system 24 generates a 2-D image 540 of an anatomical region when the X-ray source 80 of the fluoroscopy image acquisition system 24 is disposed at a first position 546 in a 3-D coordinate system of a 3-D model 542 of the anatomical region. The 2-D image 540 indicates a catheter disposed in the anatomical region.

At step 502, the computer 38 induces the display device 42 to display the 2-D image 540. The computer 38 operably communicates with the fluoroscopy image acquisition system 24, the display device 42, and the input device 44.

At step 504, a user selects a point 544 on the 2-D image 540 utilizing the input device 44 operably communicating with the display device 42. The point 544 is in a 2-D coordinate system of the 2-D image 540. The point 544 corresponds to a portion of the catheter disposed in the anatomical region.

At step 506, the computer 38 determines a first projection line 550 extending from the point 544 on the 2-D image 540 to the first position 546 of the X-ray source 80 in the 3-D coordinate system of the 3-D model 542.

At step 508, the computer 38 determines at least first and second points 552, 554 on the 3-D model 542 where the first projection line 550 intersects an outer surface of the 3-D model 550.

At step 510, the computer 38 makes a determination as to whether a user desires to select one of first and second points 552, 554. If the value of step 510 equals "yes", the method advances to step 512. Otherwise, the method advances to step 516.

At step 512, the computer 38 induces the display device 42 to display the 3-D model 542 with first and second marking icons disposed at the first and second points 552, 554, respectively. After step 512, the method advances to step 514.

At step 514, the user selects one of the first and second marking icons at the first and second points 552, 554, respectively, representing the location of the point of interest. After step 514, the method advances to step 522.

Referring again to step 510, if the value of step 510 equals "no", the method advances to step 516. At step 516, the computer 38 makes a determination as to whether the user desires automatic selection of one of first and second points 552, 554. If the value of step 516 equals "yes", the method advances to step 518. Otherwise, the method returns to step 500.

At step 518, the catheter position monitoring system 36 monitors a location of a portion of the catheter in the anatomical region. After step 518, the method advances to step 520.

At step 520, the computer 38 selects one of the first and second points 552, 554 on the 3-D model 542 of the anatomical region, based on the monitored location of the portion of the catheter in the anatomical region. After step 520, the method advances to step 522.

As discussed above, after step 514 or step 520, the method advances to step 522. At step 522, the computer 38 attaches a marking icon at the selected one of the first and second points 552, 554 representing the location of the point of interest in the 3-D model 542 of the anatomical region.

At step 524, the computer 38 induces the display device 42 to display the 3-D model 542 of the anatomical region having the marking icon at the selected one of the first and second points 552, 554 representing the location of the point of interest.

At step 526, the computer 38 stores the 3-D model 542 with the marking icon at the selected one of the first and second points 552, 554 in the memory device 40.

Referring to FIGS. 27-31, a flowchart of a method for displaying a location of electrical activation sites and voltage generation sites on a 3-D model of anatomical region of a person in accordance with another exemplary embodiment will now be explained. It should be noted that the method could be iteratively performed to display locations of a plurality of electrical activation sites on a 3-D model of an anatomical region and locations of a plurality of voltage generation sites on a 3-D model of the anatomical region.

At step 570, a user disposes the ablation-mapping catheter 32 at a first predetermined position in the heart. The ablation-mapping catheter 32 detects an electrical signal in the heart.

At step 572, the ablation-mapping catheter 32 determines a first amplitude of the electrical signal.

At step 574, the user disposes the reference catheter 34 at a second predetermined position in the heart. The reference catheter 34 detects the electrical signal in the heart.

At step 576, the fluoroscopy image acquisition system 24 generates a first 2-D image of the heart when an X-ray source 80 of the fluoroscopy image acquisition system 24 is disposed at a first position in a 3-D coordinate system of the fluoroscopy image acquisition system 24. The first 2-D image indicates the ablation-mapping catheter and the reference catheter in the heart.

At step 578, the computer 38 makes a determination as to whether a user desires to mark electrical activation sites on a 3-D model. If the value of step 578 equals "yes", the method advances to step 580. Otherwise, the method advances to step 610.

At step 580, the computer 38 induces the display device 42 to display the first 2-D image. The computer 38 operably communicates with the fluoroscopy image acquisition system 24, the display device 42, and the input device 44.

At step 582, the user selects a first point on the first 2-D image utilizing the input device 44 operably communicating with the display device 42. The first point is in a 2-D coordinate system of the first 2-D image. The first point corresponds to a portion of the ablation-mapping catheter 32 disposed in the heart.

At step 584, the computer 38 determines a first projection line extending from the first point to the first position of the X-ray source 80 in the 3-D coordinate system of the fluoroscopy image acquisition system 24.

At step 586, the fluoroscopy image acquisition system 24 generates a second 2-D image of the heart when the X-ray source 80 of the fluoroscopy image acquisition system 24 is disposed at a second position in the 3-D coordinate system of the fluoroscopy image acquisition system 24. The second 2-D image indicates the ablation-mapping catheter 32 and the reference catheter 34 in the heart.

At step 588, the computer 38 induces the display device 42 to display the second 2-D image.

At step 590, the user selects a second point on the second 2-D image utilizing the input device 44. The second point is in a 2-D coordinate system of the second 2-D image. The second point corresponds to a portion of the ablation-mapping catheter 32 disposed in the heart.

At step 592, the computer 38 determines a second projection line extending from the second point to the second position of the X-ray source 80 in the 3-D coordinate system of the fluoroscopy image acquisition system 24.

At step 594, the computer 38 determines a first point of interest in the coordinate system of the fluoroscopy image acquisition system 24 that corresponds to an intersection point of the first and second projection lines.

At step 596, the computer 38 determines a position of the first point of interest in a 3-D coordinate system of a 3-D model of the heart, utilizing a transformation matrix. The point of interest is a location of a portion of the ablation-mapping catheter 32.

At step 598, the computer 38 determines a first time that the ablation-mapping catheter 32 receives the electrical signal from the heart. The computer 38 operably communicates with the ablation-mapping catheter 32, the reference catheter 34, and the fluoroscopy image acquisition system 24.

At step 600, the computer 38 determines a second time that the ablation-mapping catheter 32 receives the electrical signal from the heart.

At step 602, the computer 38 determines a first time difference between the first and second times.

At step 604, the computer 38 attaches a first marking icon at the first point of interest in the 3-D model of the heart indicating the first time difference.

At step 606, computer 38 induces the display device 42 to display the 3-D model of the heart having the marking icon at the point of interest indicating the first time difference.

At step 608, the computer 38 stores the 3-D model with the first marking icon in the memory device 40. After step 608, the method advances to step 610.

At step 610, the computer 38 makes a determination as to whether the user desires to mark voltage generation sites on a 3-D model. If the value of step 610 equals "yes", the method advances to step 612. Otherwise, the method returns to step 576.

At step 612, the fluoroscopy image acquisition system 24 generates a third 2-D image of the heart when an X-ray source 80 of the fluoroscopy image acquisition system 24 is disposed at a third position in a 3-D coordinate system of the fluoroscopy image acquisition system 24. The third 2-D image indicates the ablation-mapping catheter 32 and the reference catheter 34 in the anatomical region.

At step 614, the computer 38 induces the display device to display the third 2-D image.

At step 616, the user selects a third point on the third 2-D image utilizing the input device 44 operably communicating with the display device 42. The third point is in a 2-D coordinate system of the third 2-D image. The third point corresponds to a portion of the ablation-mapping catheter 32 disposed in the heart.

At step 618, the computer 38 determines a third projection line extending from the third point to the third position of the X-ray source 80 in the 3-D coordinate system of the fluoroscopy image acquisition system 24.

At step 620, the fluoroscopy image acquisition system 24 generates a fourth 2-D image of the heart when the X-ray source 80 of the fluoroscopy image acquisition system 24 is disposed at a fourth position in the 3-D coordinate system of the fluoroscopy image acquisition system 24. The fourth 2-D image indicates the ablation-mapping catheter 32 and the reference catheter 34 in the heart.

At step 622, the computer 38 induces the display device 42 to display the fourth 2-D image.

At step 624, the user selects a fourth point on the fourth 2-D image utilizing the input device 44. The fourth point is in a 2-D coordinate system of the fourth 2-D image. The fourth point corresponds to a portion of the ablation-mapping catheter 32 disposed in the heart.

At step 626, the computer 38 determines a fourth projection line extending from the fourth point to the fourth position of the X-ray source 80 in the 3-D coordinate system of the fluoroscopy image acquisition system 24.

At step 628, the computer 38 determines a second point of interest in the coordinate system of the fluoroscopy image acquisition system 24 that corresponds to an intersection point of the third and fourth and second projection lines.

At step 630, the computer 38 determines a position of the second point of interest in the 3-D coordinate system of the 3-D model of the heart, utilizing a transformation matrix. The point of interest is a location of a portion of the ablation-mapping catheter 32.

At step 632, the computer 38 attaches a second marking icon at the second point of interest in the 3-D model of the heart indicating the first amplitude of the electrical signal.

At step 634, the computer 38 induces the display device 42 to display the 3-D model of the heart having the second marking icon at the second point of interest.

At step 636 the computer 38 stores the 3-D model with the second marking icon in the memory device 40.

Referring to FIG. 32, a graphical user interface 650 that is utilized to allow a user to view 2-images of anatomical regions, 3-D models of anatomical regions, and registered images of the anatomical regions is illustrated. The computer 38 can induce the display device 42 to display the graphical user interface 650. The graphical user interface 650 is also utilized to allow the user to select points on 2-D images of anatomical regions for determining points of interest on 3-D models and registered images of anatomical regions. In particular, the graphical user interface 650 allows a user to select points of interest corresponding to ablation points on a heart. As shown, the graphical user interface 650 includes a user icon 652 entitled "Ablation Points." When a user selects the user icon 652, a control panel 654 is displayed. The control panel 654 allows a user to select a plurality of ablation points 660 on the image 670.

Figure 34:
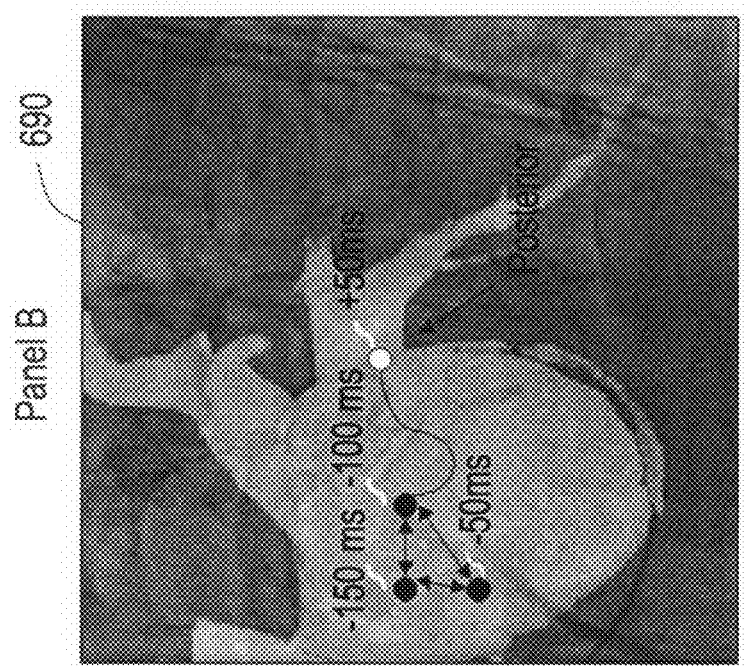
FIG. 34 is a schematic of another registered image having marked electrical activation sites.
Figure 33:
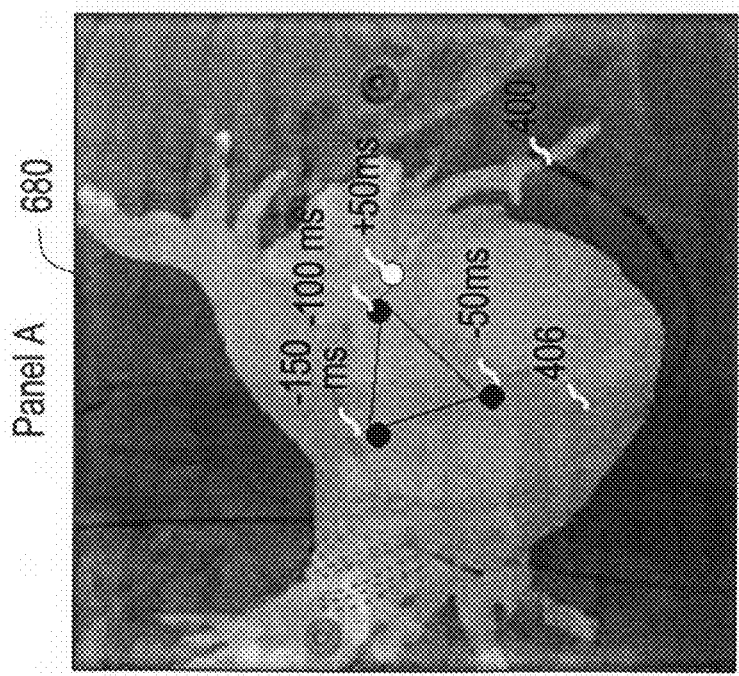
FIG. 33 is a schematic of a registered image having marked electrical activation sites.

Referring to FIG. 33, a registered image 680 having an antero-posterior view of the heart is illustrated. The registered image 680 further includes marking icons indicating positions of activation sites on a heart where the ablation-mapping catheter 32 measured an electrical signal in the heart. For example, the marking icon 682 having associated information "–150 ms" indicates that the ablation-mapping catheter 32 measured an electrical signal 150 milliseconds after the reference catheter 34 measured the electrical signal at a location in the heart corresponding to the location of the marking icon 682. Referring to FIG. 34, a registered image 690 having an anterior oblique view of the heart is illustrated. The registered image 690 further includes marking icons indicating positions of activation sites on the heart where the ablation-mapping catheter 32 measured electrical signals in the heart.

Figure 35:
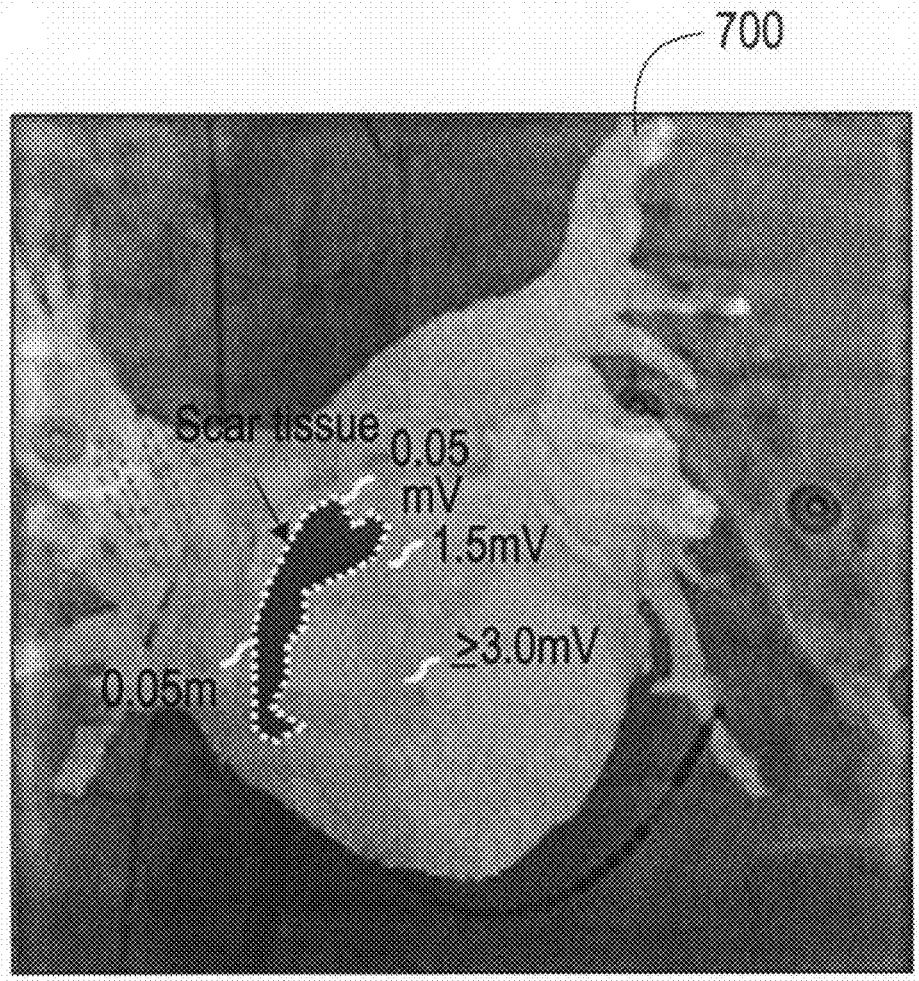
FIG. 35 is a schematic of a registered image having marked voltage generation sites.

Referring to FIG. 35, a registered image 700 having an antero-posterior view of the heart is illustrated. The registered image 700 further includes marking icons indicating positions of voltage generation sites on a heart where the ablation-mapping catheter 32 measured an amplitude of an electrical signal in the heart. For example, the marking icon 710 having associated information "1.5 mV" indicates that the ablation-mapping catheter 32 measured an electrical signal having an amplitude of 1.5 millivolts at the location in the heart identified by the marking icon 710.

The methods for displaying a location of a point of interest on a 3-D model of an anatomical region of a person represent a substantial advantage over other methods. In particular, the methods provide a technical effect of allowing a user to select at least one point on a 2-D image of an anatomical region that is automatically identified on a 3-D model of the anatomical region.

While embodiments of the invention are described with reference to the exemplary embodiments, it will be understood by those skilled in the art that various changes may be made and equivalence may be substituted for elements thereof without departing from the scope of the invention. In addition, many modifications may be made to the teachings of the invention to adapt to a particular situation without departing from the scope thereof. Therefore, it is intended that the invention not be limited to the embodiment disclosed for carrying out this invention, but that the invention includes all embodiments falling with the scope of the intended claims. Moreover, the use of the terms first, second, etc. does not denote any order of importance, but rather the terms first, second, etc. are used to distinguish one element from another. Furthermore, the use of the terms a, an, etc. do not denote a limitation of quantity, but rather denote the presence of at least one of the referenced items.

What is claimed is:

1. A method for displaying a location of a point of interest on a 3-D model of an anatomical region of a person, comprising:

determining a first projection line extending from a first point on a first 2-D image to a first position of an X-ray source, the first point being in a 2-D coordinate system of the first 2-D image, the first position being in the 3-D coordinate system of an image acquisition system;

determining a second projection line extending from a second point on a second 2-D image to a second position of the X-ray source, the second point being in a 2-D coordinate system of the second 2-D image, the second position being in the 3-D coordinate system of the image acquisition system;

determining the point of interest in the 3-D coordinate system of the image acquisition system that corresponds to an intersection point of the first and second projection lines;

determining a position of the point of interest in a 3-D coordinate system of the 3-D model of the anatomical region; and displaying the 3-D model of the anatomical region on a display device, the 3D model having a marking icon at the point of interest.

2. The method of claim 1, further comprising:

generating the first 2-D image of the anatomical region utilizing the image acquisition system when the X-ray source is disposed at the first position in a 3-D coordinate system of the image acquisition system;

selecting the first point on the first 2-D image;

generating the second 2-D image of the anatomical region utilizing the image acquisition system when the X-ray source is disposed at the second position in the 3-D coordinate system of the image acquisition system; and selecting the second point on the second 2-D image.

3. The method of claim 1, wherein determining the position of the point of interest in the 3-D coordinate system of the 3-D model of the anatomical region comprises determining the position of the point of interest in the 3-D coordinate system of the 3-D model of the anatomical region, utilizing a transformation matrix.

4. The method of claim 1, wherein the first 2-D image represents the anatomical region at a predetermined phase of a cardiac cycle and a predetermined phase of a respiratory cycle, the second 2-D image represents the anatomical region at the predetermined phase of the cardiac cycle and the predetermined phase of the respiratory cycle, and the 3-D model represents the anatomical region at the predetermined phase of the cardiac cycle and the predetermined phase of the respiratory cycle.

5. The method of claim 1, wherein the point of interest corresponds to at least one of an ablation location and a location of an electrical measurement associated with the anatomical region.

6. The method of claim 1, wherein the anatomical region is a region of a heart of the person, and the point of interest corresponds to a location of a portion of a catheter in the heart.

7. A method for displaying a location of a point of interest on a 3-D model of an anatomical region of a person, comprising:

generating a first 2-D image of the anatomical region when an X-ray source is disposed at a first position in a 3-D coordinate system of a 3-D model of the anatomical region;

selecting a first point on the first 2-D image relative to a 2-D coordinate system of the first 2-D image;

projecting the 3-D model in a first projection direction to obtain a first projected image;

determining a second point on the first projected image corresponding to the first point on the first 2-D image, utilizing a first transformation matrix;

determining a first projection line extending from the second point to the first position of the X-ray source in the 3-D coordinate system of the 3-D model;

generating a second 2-D image of the anatomical region when the X-ray source is disposed at a second position in the 3-D coordinate system of the 3-D model;

selecting a third point on the second 2-D image of the anatomical region relative to a 2-D coordinate system of the second 2-D image;

projecting the 3-D model in a second projection direction to obtain a second projected image;

determining a fourth point on the second projected image corresponding to the third point on the second 2-D image, utilizing a second transformation matrix;

determining a second projection line extending from the fourth point to the second position of the X-ray source in the 3-D coordinate system of the 3-D model;

determining the point of interest in the 3-D coordinate system of the 3-D model that corresponds to an intersection point of the first and second projection lines; and displaying the 3-D model of the anatomical region on a display device, the 3-D model having a marking icon at the point of interest.

8. The method of claim 7, wherein the first 2-D image represents the anatomical region at a predetermined phase of a cardiac cycle and a predetermined phase of a respiratory cycle, the second 2-D image represents the anatomical region at the predetermined phase of the cardiac cycle and the predetermined phase of the respiratory cycle, and the 3-D model represents the anatomical region at the predetermined phase of the cardiac cycle and the predetermined phase of the respiratory cycle.

9. The method of claim 7, wherein the point of interest corresponds to at least one of an ablation location and a location of an electrical measurement associated with the anatomical region.

10. The method of claim 7, wherein the anatomical region is a region of a heart of the person, and the point of interest corresponds to a location of a portion of a catheter in the heart.

11. A method for displaying a location of a point of interest on a 3-D model of an anatomical region of a person, comprising:

generating a 2-D image of the anatomical region utilizing an image acquisition system when an X-ray source of the image acquisition system is disposed at a first position in a 3-D coordinate system of a 3-D model of the anatomical region;

selecting a point on the 2-D image relative to a 2-D coordinate system of the 2-D image;

determining a first projection line extending from the point on the 2-D image to the first position of the X-ray source in the 3-D coordinate system of the 3-D model;

determining at least first and second points on the 3-D model where the first projection line intersects an outer surface of the 3-D model;

selecting one of the first and second points representing the location of the point of interest; and displaying the 3-D model of the anatomical region on a display device, the 3-D model having a marking icon at the selected one of the first and second points representing the point of interest.

12. The method of claim 11, wherein selecting one of the first and second points representing the location of the point of interest comprises selecting one of the first and second points representing the location of the point of interest, utilizing an input device.

13. The method of claim 11, further comprising monitoring a location of a portion of a catheter in the anatomical region, utilizing a position monitoring system, wherein selecting one of the first and second points representing the location of the point of interest includes selecting one of the first and second points that corresponds to the monitored location of the portion of the catheter.

14. The method of claim 11, wherein the 2-D image represents the anatomical region at a predetermined phase of a cardiac cycle and a predetermined phase of a respiratory cycle, and the 3-D model represents the anatomical region at the predetermined phase of the cardiac cycle and the predetermined phase of the respiratory cycle.

15. The method of claim 11, wherein the point of interest corresponds to at least one of an ablation location and a location of an electrical measurement associated with the anatomical region.

16. The method of claim 11, wherein the anatomical region is a region of a heart of the person, and the point of interest corresponds to a location of a portion of a catheter in the heart.

* * * * *

UNITED STATES PATENT AND TRADEMARK OFFICE
CERTIFICATE OF CORRECTION

PATENT NO. : 7,995,819 B2  Page 1 of 6
APPLICATION NO. : 11/928759
DATED : August 9, 2011
INVENTOR(S) : Vaillant et al.

It is certified that error appears in the above-identified patent and that said Letters Patent is hereby corrected as shown below:

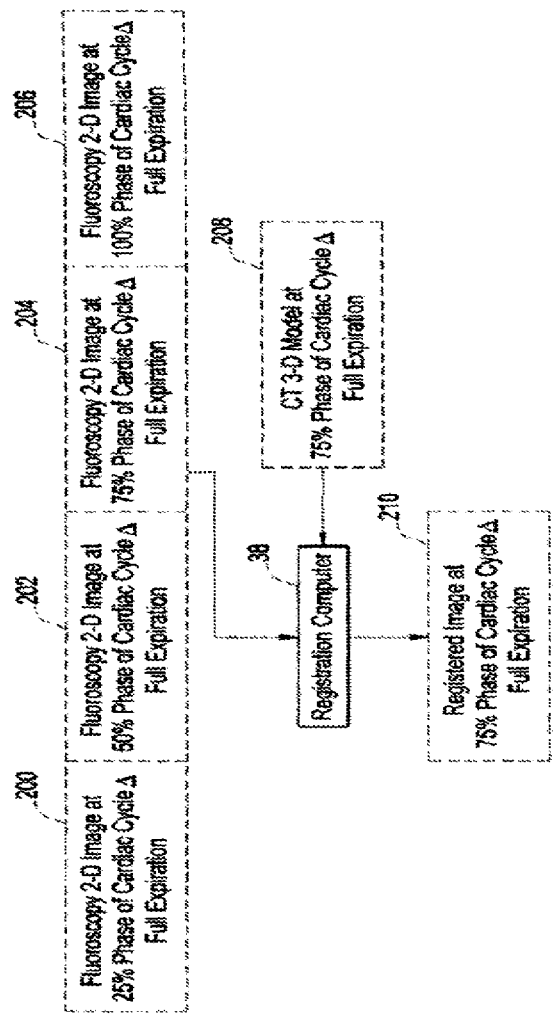

In Fig. 8, Sheet 6 of 29, delete "                                                                                              "

Signed and Sealed this
Twenty-seventh Day of March, 2012

David J. Kappos
*Director of the United States Patent and Trademark Office*

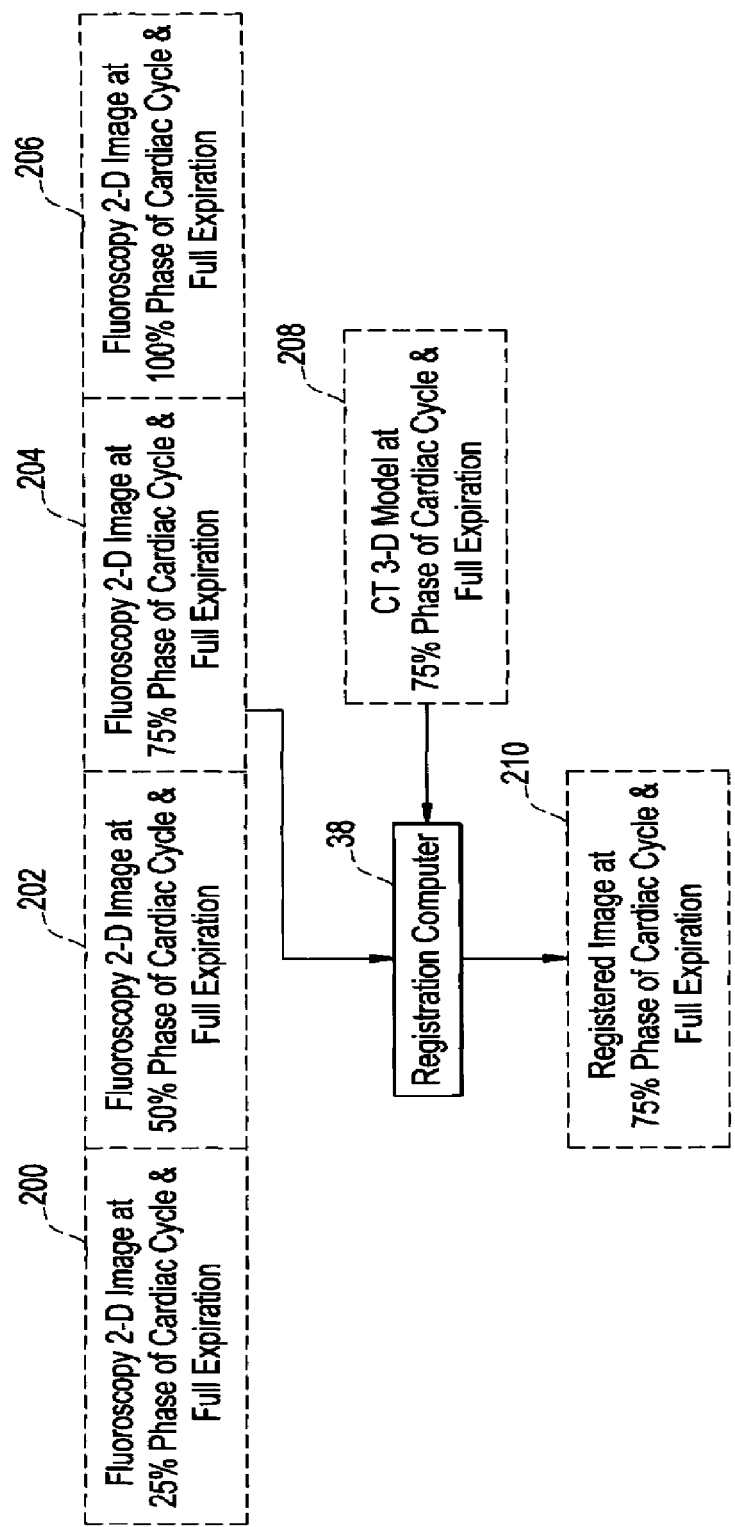
and insert --
therefor.

In Fig. 17, sheet 12 of 29, delete
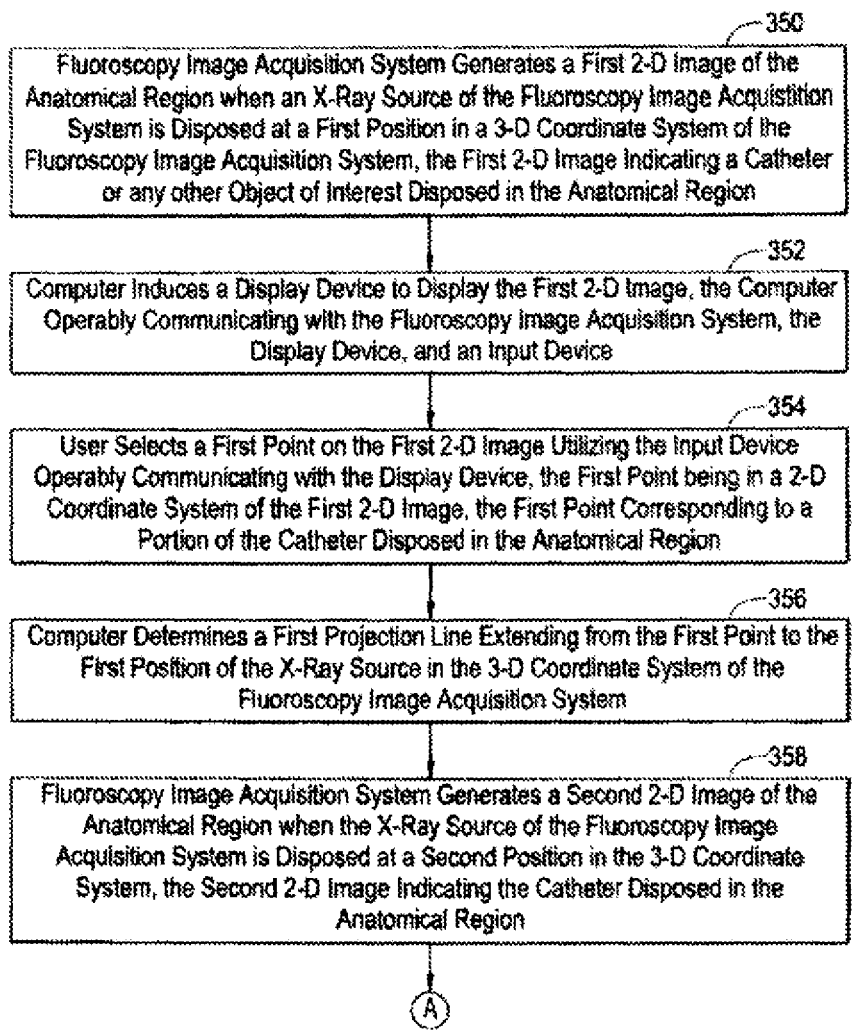
"
"

and insert --
therefor.

--,

CERTIFICATE OF CORRECTION (continued)
U.S. Pat. No. 7,995,819 B2

Figure 22:
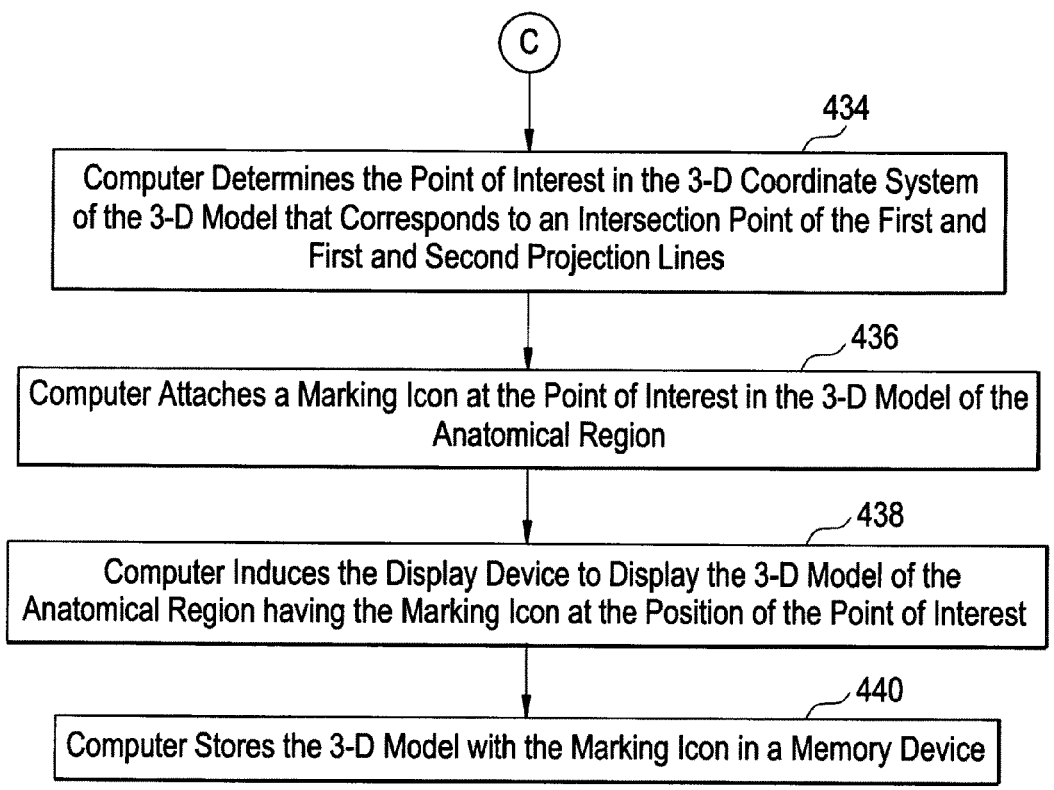
Figure 23:
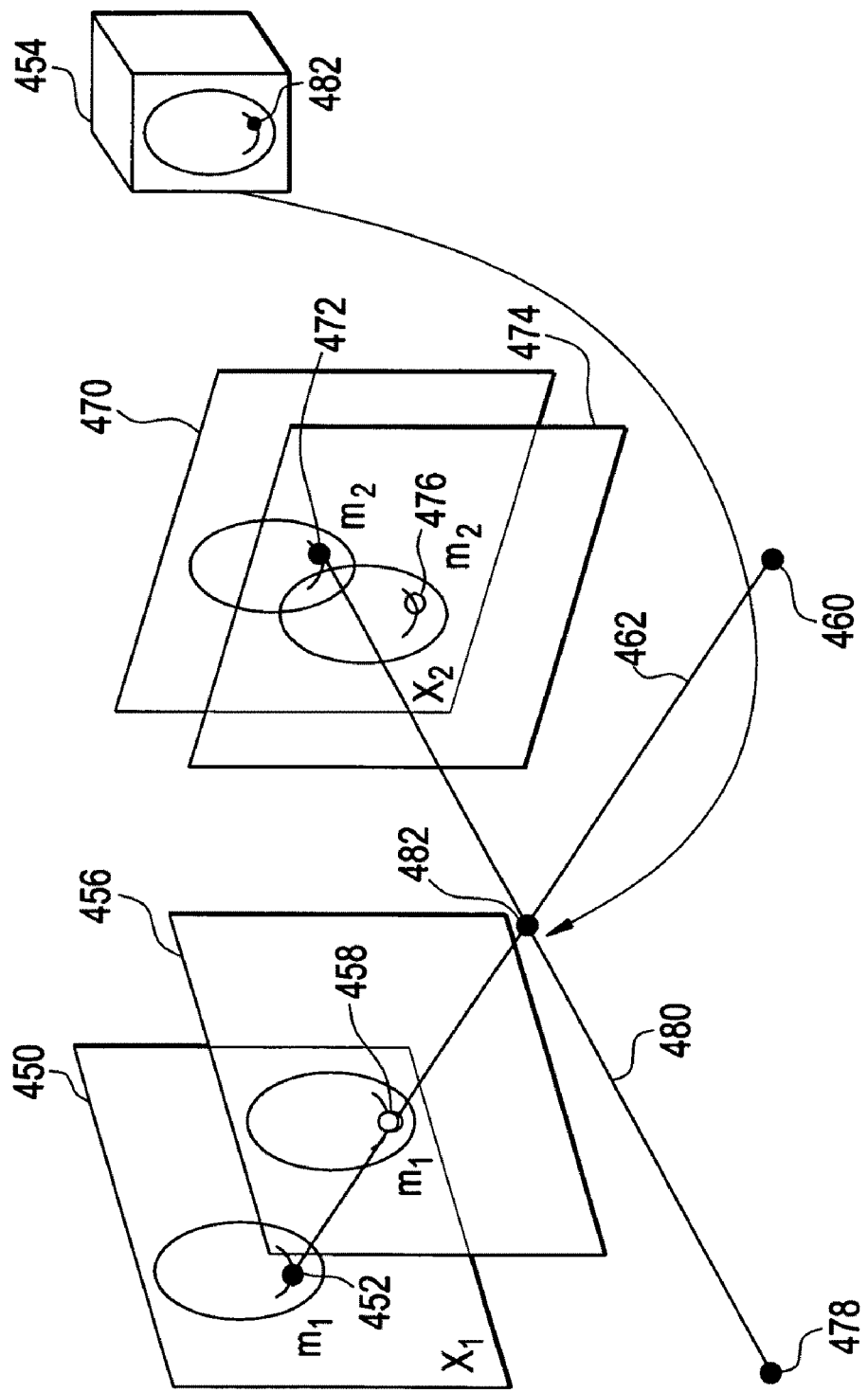
FIG. 23 is a schematic of exemplary 2-images and a 3-model utilized in the method of FIGS. 20-22.

In Fig. 22, sheet 5 of 29, delete

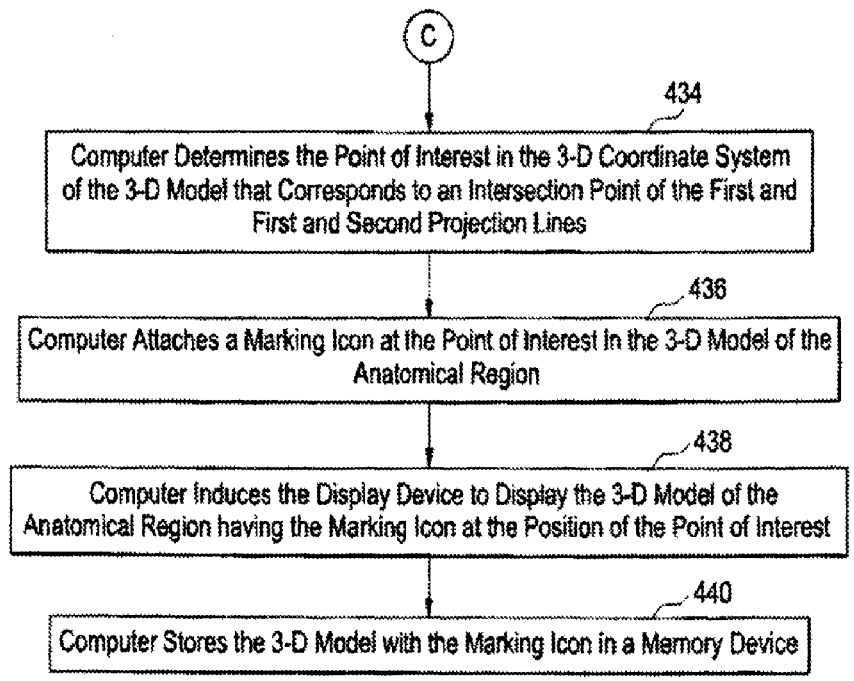

and insert

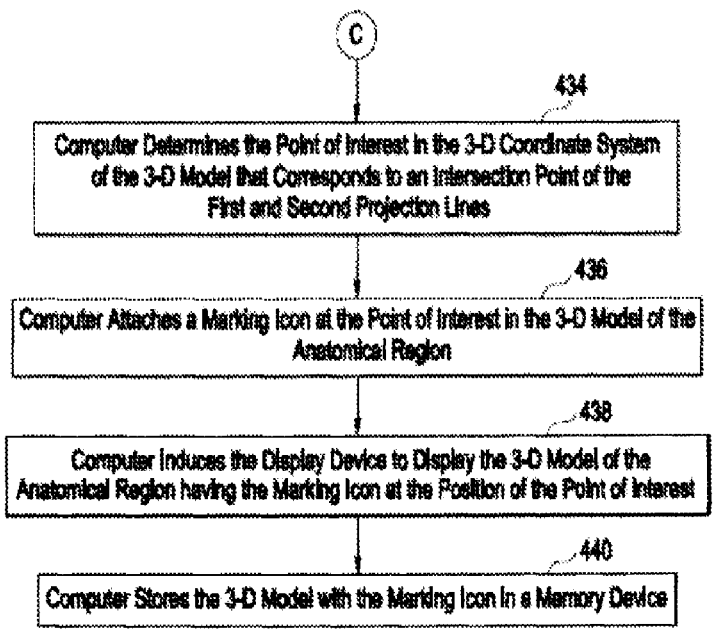

therefor.

In Fig. 35, sheet 29 of 29, delete

Antero posterior view

" and insert

Antero posterior view

-- --, therefor.